United States Patent [19]
Mahurkar

[11] Patent Number: 5,514,100
[45] Date of Patent: May 7, 1996

[54] HYPODERMIC NEEDLE ASSEMBLY

[76] Inventor: Sakharam D. Mahurkar, 6171 N. Sheridan Rd., #1112, Chicago, Ill. 60660

[21] Appl. No.: 229,811

[22] Filed: Apr. 19, 1994

Related U.S. Application Data

[62] Division of Ser. No. 111372, Aug. 23, 1993, Pat. No. 5,338,311.

[51] Int. Cl.$^6$ ............................. A61M 5/32; A61M 31/00
[52] U.S. Cl. ............................. 604/195; 604/53; 604/158
[58] Field of Search ............................. 604/53, 158, 164, 604/165, 188, 194, 195, 196, 198, 240, 242; 128/763–766

[56] References Cited

U.S. PATENT DOCUMENTS

| | | | |
|---|---|---|---|
| Des. 298,352 | 11/1988 | Raines . | |
| 2,888,923 | 6/1959 | Cunha Reis | 604/194 |
| 2,925,083 | 12/1957 | Craig . | |
| 3,610,240 | 6/1967 | Harautuneian . | |
| 3,658,061 | 4/1975 | Hall . | |
| 4,068,659 | 1/1978 | Moorehead | 604/53 |
| 4,233,982 | 11/1980 | Bauer et al. . | |
| 4,245,635 | 1/1981 | Kontos . | |
| 4,261,357 | 4/1981 | Kontos . | |
| 4,274,408 | 6/1981 | Nimrod . | |
| 4,417,886 | 11/1983 | Frankhouser et al. | 604/53 |
| 4,424,833 | 1/1984 | Spector et al. . | |
| 4,425,120 | 1/1984 | Sampson et al. . | |
| 4,468,224 | 8/1984 | Enzmann et al. . | |
| 4,529,399 | 7/1985 | Groshong et al. . | |

(List continued on next page.)

FOREIGN PATENT DOCUMENTS

| | | |
|---|---|---|
| 2004771 | 11/1969 | France . |
| 2415196 | 10/1975 | Germany . |
| 2507119 | 9/1976 | Germany . |
| 3042229 | 5/1982 | Germany . |

OTHER PUBLICATIONS

"Health Care" by Helene Cooper, Wall Street Journal (Nov. 25, 1992).
The G.M.P. Letter (May 1992).
Devices & Diagnostics Letter, vol. 19, No. 19 (May 8, 1992).
FDA Medical Bulletin, vol. 22, No. 2 (Sep. 22, 1992).
"Safer Syringes Boost Molder Opportunities" by Carl Kirkland, Plastic World, vol. 51/No. 8, pp. 20–24, (Aug. 1993).
"Ultrasonic Get Medical Seal Of Approval" by Marcie Moskowitz, Plastic World, vol. 51/No. 8, pp. 26–28, (Aug. 1993).
Brochure for Arrow® Ravelerson Syringe.
Brochure for Syringes by Becton Dickinson of Franklin Lake, New Jersey (1992).
Devices & Diagnostics Letter, p. 2 (Aug. 21, 1992).
Chiarello, Linda A., "Reducing Needlestick Injuries among Health Care Workers" AIDS Clinical Care Oct. 1993 vol. 5 No. 10 Mass. Medical Society.

*Primary Examiner*—C. Fred Rosenbaum
*Assistant Examiner*—Frank Wilkens, III
*Attorney, Agent, or Firm*—Arnold, White & Durkee

[57] ABSTRACT

A needle-syringe assembly, operable in a normal mode and convertible to a retraction mode, comprises an elongated, generally cylindrical barrel, a plunger slidably mounted in the barrel, and a needle holder carrying a hollow needle on the distal end thereof. The barrel forms a hollow nozzle located at the distal end of the barrel. The plunger forms a coaxial cavity extending therethrough, and the plunger includes a helical slot exposing a proximal portion of the coaxial cavity. The needle holder is slidably mounted in the coaxial cavity of the plunger. During the normal mode, a distal portion of the needle holder is engaged within the nozzle by a taper lock. To switch from the normal mode to the retraction mode, the taper lock is disengaged by rotary movement of the plunger relative to the barrel. While preventing rotary movement of the needle holder relative to the barrel, continued rotary movement of the plunger causes a lateral arm of the needle holder to ascend through the helical slot so that the needle holder retracts into the coaxial cavity of the plunger and the needle is concealed.

42 Claims, 20 Drawing Sheets

U.S. PATENT DOCUMENTS

| | | |
|---|---|---|
| 4,631,057 | 12/1986 | Mitchell . |
| 4,659,330 | 4/1987 | Nelson et al. . |
| 4,664,654 | 5/1987 | Strauss . |
| 4,666,435 | 5/1987 | Braginetz . |
| 4,693,708 | 9/1987 | Wanderer et al. . |
| 4,702,738 | 10/1987 | Spencer . |
| 4,710,170 | 12/1987 | Haber et al. . |
| 4,731,059 | 3/1988 | Wanderer et al. . |
| 4,731,068 | 3/1988 | Hesse . |
| 4,732,162 | 3/1988 | Martell . |
| 4,735,617 | 4/1988 | Nelson et al. . |
| 4,735,618 | 4/1988 | Hagen . |
| 4,742,910 | 5/1988 | Staebler . |
| 4,746,017 | 5/1988 | Howard et al. . |
| 4,747,831 | 5/1988 | Kulli . |
| 4,747,835 | 5/1988 | Sandhaus . |
| 4,747,836 | 5/1988 | Luther . |
| 4,752,290 | 6/1988 | Schramm . |
| 4,762,516 | 8/1988 | Luther et al. . |
| 4,767,412 | 8/1988 | Hymanson . |
| 4,767,413 | 8/1988 | Haber et al. . |
| 4,778,453 | 10/1988 | Lopez . |
| 4,782,841 | 11/1988 | Lopez . |
| 4,790,822 | 12/1988 | Haining . |
| 4,799,926 | 1/1989 | Haber . |
| 4,801,295 | 1/1989 | Spencer . |
| 4,808,169 | 2/1989 | Haber et al. . |
| 4,813,426 | 3/1989 | Haber et al. . |
| 4,813,938 | 3/1989 | Raulerson . |
| 4,816,024 | 3/1989 | Sitar et al. . |
| 4,819,659 | 4/1989 | Sitar . |
| 4,826,488 | 5/1989 | Nelson et al. . |
| 4,826,489 | 5/1989 | Haber et al. . |
| 4,826,491 | 5/1989 | Schramm . |
| 4,828,107 | 5/1989 | Spencer . |
| 4,828,548 | 5/1989 | Walter . |
| 4,832,696 | 5/1989 | Luther et al. . |
| 4,834,717 | 5/1989 | Haber et al. . |
| 4,838,871 | 6/1989 | Luther . |
| 4,842,591 | 6/1989 | Luther . |
| 4,846,811 | 7/1989 | Vanderhoof . |
| 4,850,961 | 7/1989 | Wanderer et al. . |
| 4,850,976 | 6/1989 | Heinrich et al. . |
| 4,852,584 | 8/1989 | Selby . |
| 4,863,435 | 9/1989 | Sturman et al. . |
| 4,863,436 | 9/1989 | Glick . |
| 4,872,552 | 10/1989 | Unger . |
| 4,874,384 | 10/1989 | Nunez . |
| 4,883,469 | 11/1989 | Glazier . |
| 4,887,998 | 12/1989 | Martin et al. . |
| 4,892,525 | 1/1990 | Hermann, Jr. et al. . |
| 4,894,055 | 1/1990 | Sudnak . |
| 4,897,083 | 1/1990 | Martell . |
| 4,898,588 | 2/1990 | Roberts . |
| 4,900,311 | 2/1990 | Stern et al. . |
| 4,903,832 | 2/1990 | Stewart . |
| 4,906,235 | 3/1990 | Roberts . |
| 4,909,794 | 3/1990 | Haber et al. . |
| 4,911,693 | 3/1990 | Paris . |
| 4,915,696 | 4/1990 | Feimer . |
| 4,915,697 | 4/1990 | DuPont . |
| 4,917,673 | 4/1990 | Coplin . |
| 4,919,656 | 4/1990 | Bracker et al. . |
| 4,927,019 | 5/1990 | Haber et al. . |
| 4,927,417 | 5/1990 | Moncada et al. . |
| 4,928,824 | 5/1990 | Barasch . |
| 4,929,241 | 5/1990 | Kulli . |
| 4,931,040 | 6/1990 | Haber et al. . |
| 4,931,048 | 6/1990 | Lopez . |
| 4,932,940 | 6/1990 | Walker et al. . |
| 4,932,946 | 6/1990 | Shields . |
| 4,935,015 | 6/1990 | Hall . |
| 4,944,723 | 7/1990 | Haber et al. . |
| 4,944,728 | 7/1990 | Carrell et al. . |
| 4,944,731 | 7/1990 | Cole . |
| 4,946,447 | 8/1990 | Hardcastle et al. . |
| 4,950,241 | 8/1990 | Ranford . |
| 4,950,252 | 8/1990 | Luther et al. . |
| 4,958,622 | 9/1990 | Selenke . |
| 4,964,854 | 10/1990 | Luther . |
| 4,973,316 | 11/1990 | Dysarz . |
| 4,976,702 | 12/1990 | Andrews et al. . |
| 4,986,813 | 1/1991 | Blake, III et al. . |
| 4,986,819 | 1/1991 | Sobel . |
| 4,988,339 | 1/1991 | Vadher . |
| 4,994,042 | 2/1991 | Vadher . |
| 4,994,044 | 2/1991 | LoDuca . |
| 4,997,422 | 3/1991 | Chow et al. . |
| 5,000,167 | 3/1991 | Sunderland . |
| 5,002,536 | 3/1991 | Thompson et al. . |
| 5,013,304 | 5/1991 | Russell et al. . |
| 5,015,241 | 5/1991 | Feimer . |
| 5,019,045 | 5/1991 | Lee . |
| 5,019,051 | 5/1991 | Hake . |
| 5,024,326 | 6/1991 | Sandel et al. . |
| 5,024,660 | 6/1991 | McNaughton . |
| 5,026,345 | 6/1991 | Teringo . |
| 5,026,354 | 6/1991 | Kocses . |
| 5,030,209 | 7/1991 | Wanderer et al. . |
| 5,030,212 | 7/1991 | Rose . |
| 5,037,400 | 8/1991 | Curry . |
| 5,037,401 | 8/1991 | DeCamp . |
| 5,045,062 | 9/1991 | Henson . |
| 5,046,508 | 9/1991 | Weissler . |
| 5,049,136 | 9/1991 | Johnson . |
| 5,051,109 | 9/1991 | Simon . |
| 5,053,017 | 10/1991 | Chamuel . |
| 5,057,088 | 10/1991 | Narayanan et al. . |
| 5,057,089 | 10/1991 | Greco . |
| 5,059,180 | 10/1991 | McLees . |
| 5,061,249 | 10/1991 | Campbell . |
| 5,066,279 | 11/1991 | Russell . |
| 5,066,281 | 11/1991 | Stevenson-Michener . |
| 5,067,942 | 11/1991 | Jaffe et al. . |
| 5,067,944 | 11/1991 | Nichols . |
| 5,067,946 | 11/1991 | Zhadanov . |
| 5,067,949 | 11/1991 | Freundlich et al. . |
| 5,069,669 | 12/1991 | Kole . |
| 5,078,693 | 1/1992 | Shine . |
| 5,084,019 | 1/1992 | Gartz . |
| 5,086,780 | 2/1992 | Schmitt ................ 604/194 |
| 5,088,987 | 2/1992 | Noonan, Jr. . |
| 5,088,988 | 2/1992 | Talonn et al. . |
| 5,092,853 | 3/1992 | Couvertier, II . |
| 5,098,394 | 3/1992 | Luther . |
| 5,098,402 | 3/1992 | Davis . |
| 5,106,379 | 4/1992 | Leap . |
| 5,106,380 | 4/1992 | Lobello . |
| 5,108,378 | 4/1992 | Firth et al. . |
| 5,112,307 | 5/1992 | Haber et al. . |
| 5,112,315 | 5/1992 | Gloyer et al. . |
| 5,114,404 | 5/1992 | Paxton et al. . |
| 5,116,325 | 5/1992 | Paterson . |
| 5,120,309 | 6/1992 | Watts . |
| 5,122,118 | 6/1992 | Haber et al. . |
| 5,125,898 | 6/1992 | Haufhold, Jr. et al. . |
| 5,127,910 | 7/1992 | Talonn et al. . |
| 5,135,504 | 8/1992 | McLees . |
| 5,135,505 | 8/1992 | Kaufman . |
| 5,147,326 | 9/1992 | Talonn et al. . |
| 5,160,326 | 11/1992 | Talonn et al. . |
| 5,163,908 | 11/1992 | Lambert . |

| | | | | | |
|---|---|---|---|---|---|
| 5,163,917 | 11/1992 | Huefner et al. . | 5,201,718 | 4/1993 | Whisson ................................. 604/194 |
| 5,171,300 | 12/1992 | Blake, III et al. . | 5,215,524 | 6/1993 | Vallelunga et al. . |
| 5,171,303 | 12/1992 | DeCamp . | 5,215,525 | 6/1993 | Sturman . |
| 5,176,640 | 1/1993 | Nacci et al. . | 5,215,528 | 6/1993 | Purdy et al. . |
| 5,176,655 | 1/1993 | McCormick et al. . | 5,215,529 | 6/1993 | Fields et al. . |
| 5,181,524 | 1/1993 | Wanderer et al. . | 5,215,533 | 6/1993 | Robb . |
| 5,183,468 | 2/1993 | McLees . | 5,215,534 | 6/1993 | De Harde et al. . |
| 5,188,119 | 2/1993 | Sunderland . | 5,215,535 | 6/1993 | Gettig et al. . |
| 5,188,611 | 2/1993 | Orgain . | 5,215,536 | 6/1993 | Lampropoulous . |
| 5,188,613 | 2/1993 | Shaw . | 5,217,436 | 6/1993 | Farkas . |
| 5,190,526 | 3/1993 | Murray et al. . | 5,217,437 | 6/1993 | Talonn et al. . |
| 5,190,532 | 3/1993 | Yu . | 5,219,333 | 6/1993 | Sagstetter et al. . |
| 5,195,973 | 3/1993 | Novick . | 5,219,338 | 6/1993 | Haworth . |
| 5,195,975 | 3/1993 | Castagna . | 5,221,262 | 6/1993 | Kite . |
| 5,195,982 | 3/1993 | Hoenig . | 5,222,942 | 6/1993 | Bader . |
| 5,195,983 | 3/1993 | Boese . | 5,222,943 | 6/1993 | Mazzara . |
| 5,195,992 | 3/1993 | Dudar et al. . | 5,222,944 | 6/1929 | Harris . |
| 5,195,993 | 3/1993 | Gianakos . | 5,222,945 | 6/1993 | Basnight . |
| 5,197,953 | 3/1993 | Colonna . | 5,222,947 | 6/1993 | D'Amico . |
| 5,197,954 | 3/1993 | Cameron . | | | |

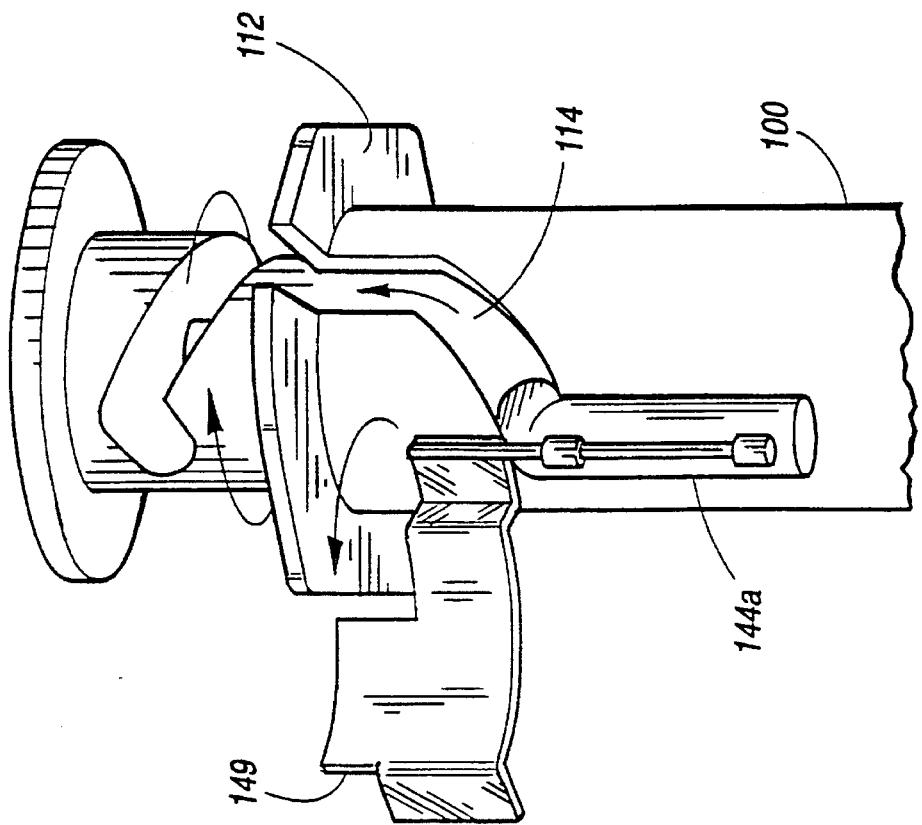
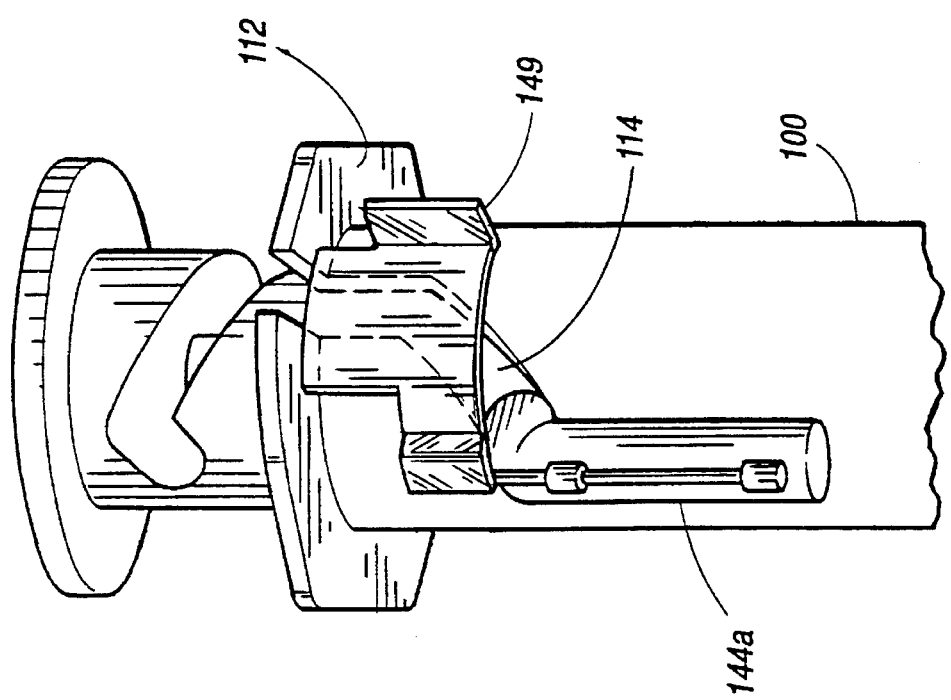

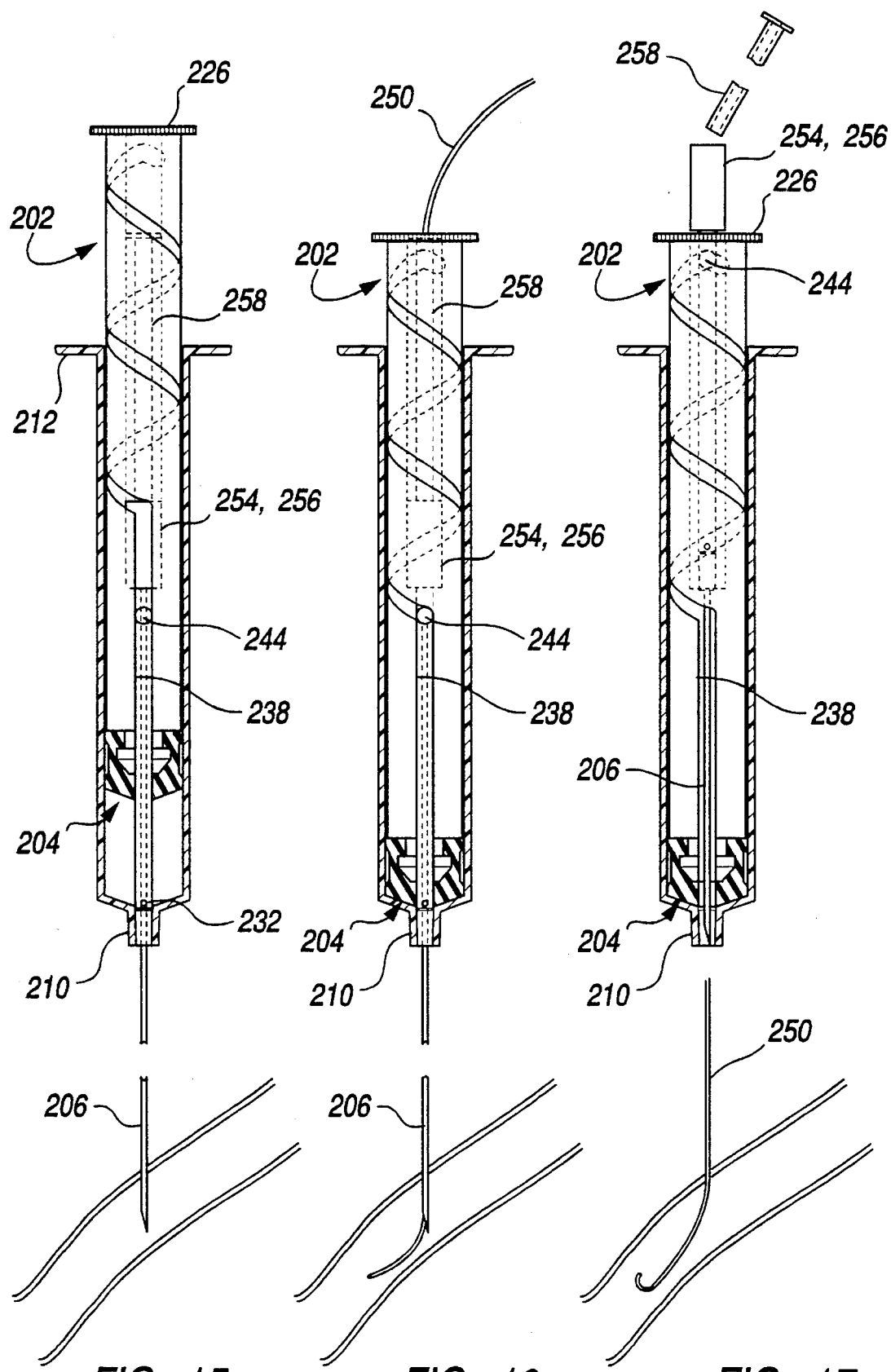

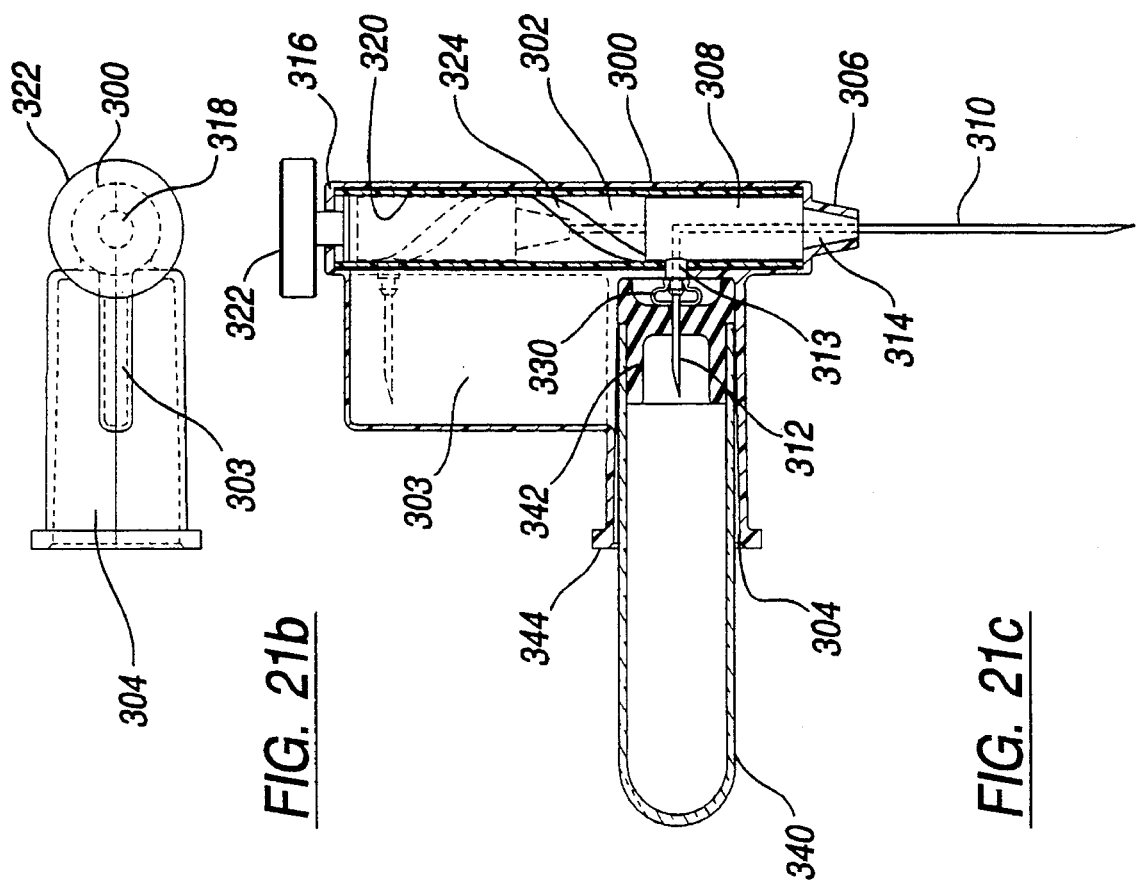
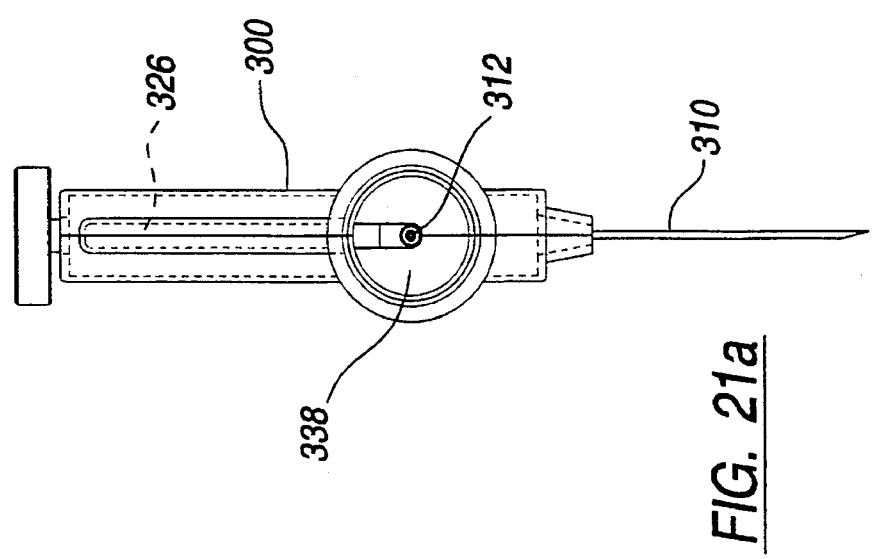
FIG. 21b
FIG. 21c
FIG. 21a

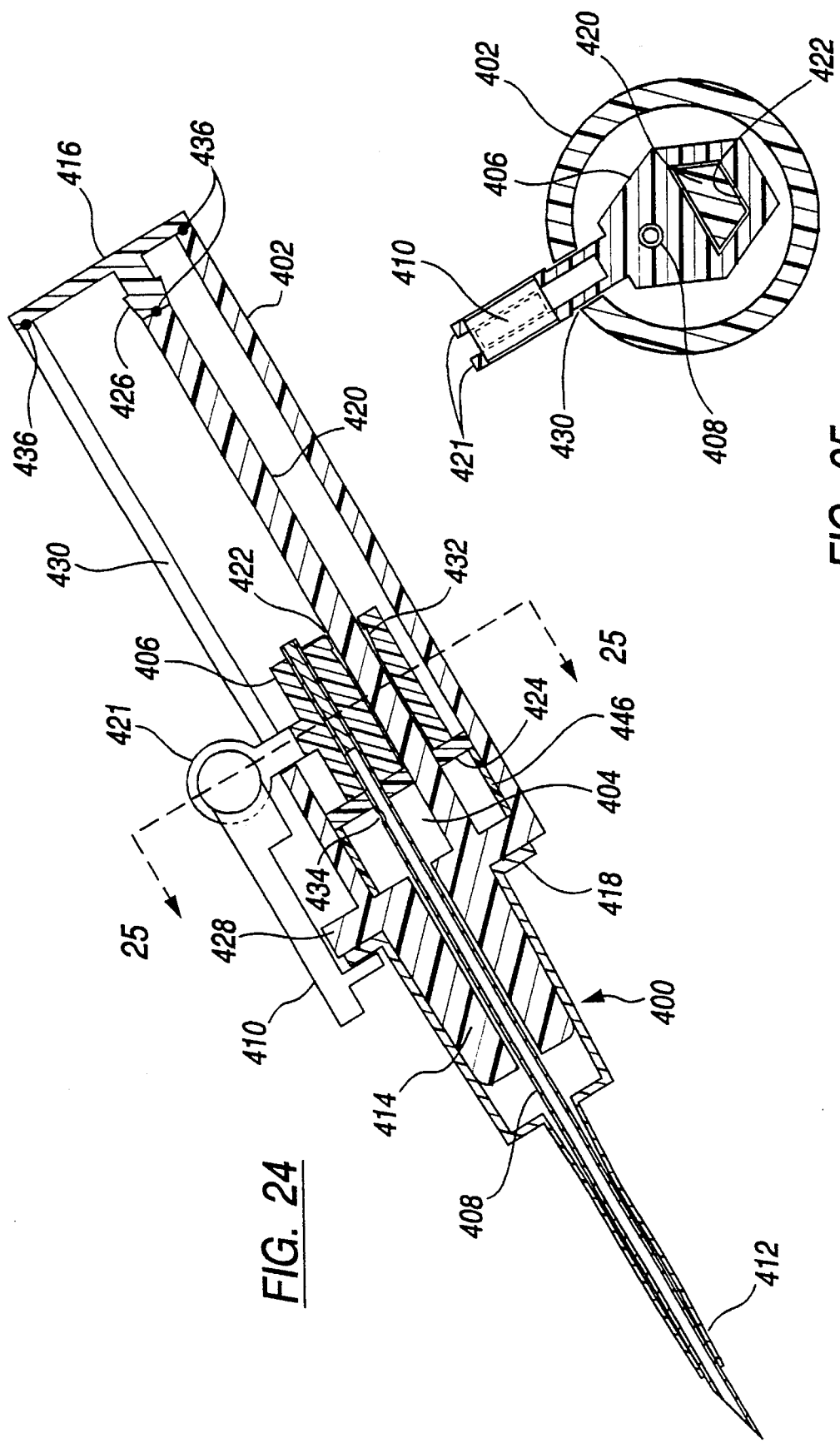

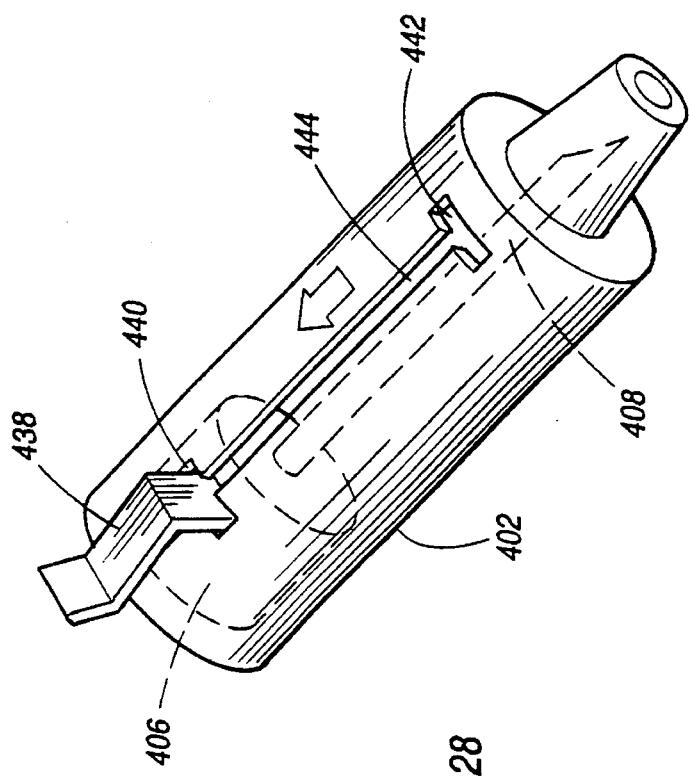
FIG. 29
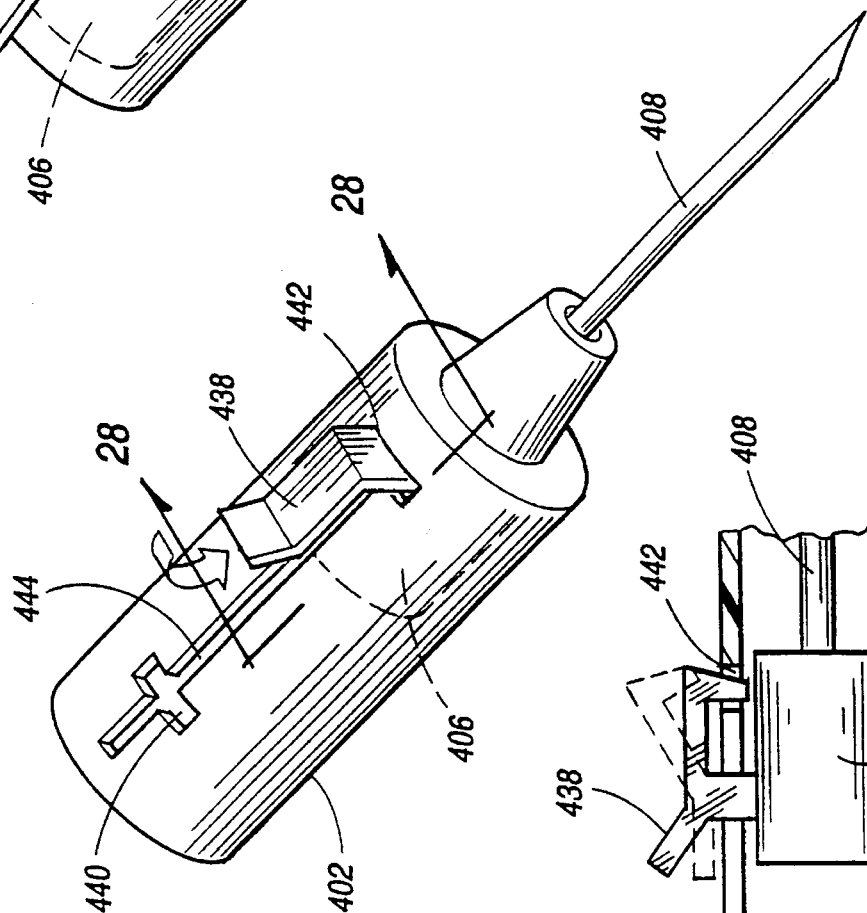
FIG. 27
FIG. 28

HYPODERMIC NEEDLE ASSEMBLY

This application is a divisional of application Ser. No. 08/111,372, filed Aug. 23, 1993 now U.S. Pat. No. 5,338, 311.

FIELD OF THE INVENTION

The present invention generally relates to hypodermic needles. In particular, the present invention relates to various needle assemblies which conceal the sharp point of the hypodermic needle following use.

BACKGROUND OF THE INVENTION

A hypodermic needle has many applications in modem medicine. One application is to fit the hypodermic needle into a syringe and to then insert the needle into a person's body for intra-muscular, subcutaneous, or intravenous injection of medications. Another application of the hypodermic needle is to introduce a guidewire into a central vein of a person. The hypodermic needle acts as a sharp introducing instrument through which the guidewire is advanced into the vein of the patient. Following insertion of the guidewire, the needle is removed and a catheter is threaded over the guidewire and, when in place, used for diagnostic monitoring or for therapeutic procedures such as hemodialysis. Yet another application is to collect blood samples for tests using a hypodermic needle with two sharp puncturing beveled ends mounted on the barrel of a syringe. The distal puncturing end of the needle is inserted into a person's vein while an inverted rubber-capped vacuum tube is pushed into the barrel so that the other end of the needle pierces the rubber cap of the vacuum tube. Thus, a blood sample passes from the vein, through the needle, and into the vacuum tube. A fourth application of the hypodermic needle is to coaxially mount a catheter over a hypodermic needle and to puncture a vein of a person's body with the needle. Following needle puncture, the over-the-needle ("OTN") catheter is advanced into the vein, the needle is removed, and the catheter is connected to an intravenous line for fluid infusions into the vein. The foregoing applications constitute the most common applications of hypodermic needles.

A hypodermic needle entering into a patient's body is invariably contaminated by the patient's blood and body fluids. Following use of the needle, the needle presents a risk to physicians, nurses, and other health care personnel because the needle might transmit an infection or disease to such personnel if it were to accidently puncture them. Thus, health care personnel are in constant danger of contracting infections and diseases, some of which may be deadly. Other potential victims of accidental needle punctures include sanitation workers which later dispose of garbage containing the hypodermic needle. The diseases which may be transmitted by a contaminated hypodermic needle include Immune Deficiency Virus, Hepatitis, Rabies, Kure, Encephalitis, and Arbor viruses. The outcome of contracting one of these diseases is often fatal because there are no known cures for any of these diseases. Often a needle puncture in a person's skin is so trivial that it remains unrecognized until the person becomes seriously ill.

The problem of suffering accidental needle punctures is well recognized. As a result, enormous inventive effort has been devoted to concealing the sharp needle point of hypodermic needles. Despite this effort, the prevalence and magnitude of needle prick-transmitted diseases is still high, as reflected in such recent articles as "Health Care" by Helene Cooper, Wall Street Journal (Nov. 25, 1992); The G.M.P. Letter (May, 1992); Devices & Diagnostics Letter, Vol. 19, No. 19 (May 8, 1992); and FDA Medical Bulletin, Vol. 22, No. 2 (Sep. 22, 1992).

In order to avoid the transmittal of disease by needle punctures, efforts have been directed to preventing exposure of the sharp point of the hypodermic needle. One approach is to cap the needle following use. This approach, however, presents a risk of danger because it involves placing the fingers directly opposite to the needle point. To help keep the fingers away from the needle point while capping the needle, needle caps provided with wide mouths or long handles have been developed by others. Examples of such needle caps are described in U.S. Pat. Nos. 4,735,617; 4,742,910; 4,747, 835; 4,767,412; 4,850,976; 4,852,584; 4,892,525; 4,906, 235; 4,919,656; 4,928,824; 4,958,622; 5,066,279; 5,190, 532; and 5,195,982. While the foregoing needle caps reduce the risk of suffering a needle prick, this approach still requires a person to place his/her fingers near the needle and such finger placement is an active invitation to a needle prick. It cannot be over emphasized that even a single contaminated needle prick is unacceptable.

Another approach to concealing hypodermic needles following use is to provide safe disposal containers as described in U.S. Pat. Nos. 4,746,017; 4,828,107; 4,903, 832; 4,994,044; 5,024,326; and 5,067,949. Such safety containers, however, do not solve the problem because needle pricks can and do occur even before the hypodermic needles reach their final disposal destination in the safety containers.

DESCRIPTION OF RELATED ART

In addition to the above approaches to preventing needle pricks, specific approaches have been taken to prevent needle pricks in each of the aforementioned applications for hypodermic needles, as summarized below in detail.

First, with respect to syringes fitted with hypodermic needles for injection of medications, one approach to preventing a needle prick from a syringe is to provide the barrel of the syringe with a mounted reciprocating barrel, sleeve, sheath, guard, protector, or the like which is slidable and lockable in a forward position over the needle by detentes. The sleeve is either manually slid over the hypodermic needle following use of the needle or automatically actuated by latches and springs. Examples of coaxial sleeves for syringes are described in U.S. Pat. Nos. 2,925,083; 4,425, 120; 4,631,057; 4,666,435; 4,693,708; 4,702,738; 4,752, 290; 4,801,295; 4,826,488; 4,826,491; 4,900,311; 4,917, 673; 4,927,417; 4,932,940; 4,946,447; 4,976,702; 4,988, 339; 4,997,422; 5,015,241; 5,019,051; 5,024,660; 5,057, 088; 5,057,089; 5,088,988; 5,106,379; 5,106,380; 5,108, 378; 5,112,307; 5,120,309; 5,127,910; 5,147,326, 5,160, 326; 5,163,917; 5,195,993; and 5,197,953. Furthermore, examples of coaxial sleeves are marketed by Becton Dickinson of Franklin Lakes, N.J., and Sherwood Medical of St. Louis, Mo. Examples of reciprocating non-coaxial sleeves are described in U.S. Pat. Nos. 4,659,330; 4,915,696; 4,986, 819; and 5,013,304.

A problem with using a coaxial or non-coaxial sleeve to cover the hypodermic needle of a syringe is that addition of the sleeve makes the syringe bulky, and the sleeve may impair the readability of the volume markings on the barrel of the syringe. Moreover, while attempting to insert the hypodermic needle into a person's body, the slidable sleeve often does not provide an adequate grip for penetration force because the sleeve tends to slip. In addition, the sleeve may disturb the insertion angle for penetration. Another problem is that the sliding and locking detentes may become dislodged so as to expose the needle covered by the sleeve. Finally, the sleeve increases the bulk of disposal following use of the syringe.

Another approach to concealing the hypodermic needle of a syringe is to mount a protective coaxial sleeve directly on the needle itself. Examples of such sleeves are described in U.S. Pat. Nos. 4,664,654; 4,778,453; 4,863,435; 4,863,436; 4,894,055; 4,897,083; 4,911,693; 4,915,697; 4,931,048; and 5,195,983. In addition to making the syringe more bulky, a needle-mounted sleeve requires a longer needle and this interferes with the transmission of insertion force at the tip of the needle. Other patents, such as U.S. Pat. Nos. 4,872,552, 4,883,469, and 4,932,946, disclose a protective sleeve attached to a hypodermic needle by a hinge. Like the needle-mounted coaxial sleeve, the hinged sleeve makes the syringe bulky and interferes with needle insertion. U.S. Pat. No. 5,197,954 describes a syringe with a hinged hypodermic needle that can be folded inside a guard molded to the side of the barrel. Attempts to fold the needle inside the guard, however, present a danger of needle pricks.

Unsatisfied with the sliding or hinged protective sleeve, other inventors have envisioned that the hypodermic needle of the syringe should be locked in and shielded by the syringe barrel itself. In such syringes, the needle is typically fixed in an insert which is slidable in the nozzle mounted on the distal end of the syringe barrel. The insert as well as the distal end of the plunger is equipped with some type of mechanical coupling or actuator. Following injection of medicine with the advancing plunger, the insert is coupled to the distal end of the plunger so that retraction of the plunger causes retraction of the needle inside the syringe barrel. Locking is complete when a portion of the plunger is engaged to the margin of the barrel and broken off. Mechanical couplings such as that described above are disclosed in U.S. Pat. Nos. 4,710,170; 4,790,822; 4,935,015; 4,944,723; 4,950,241; 4,986,813; 5,026,354; 5,061,249; 5,066,281; 5,098,402; 5,112,315; 5,114,404; 5,122,118; 5,171,300; 5,176,640; and 5,188,613. Similar results are achieved using spring-loaded mechanisms, as described in U.S. Pat. Nos. 4,767,413; 4,973,316; and 5,046,508. Furthermore, U.S. Pat. No. 5,125,898 to Kaufhold Jr. et al. discloses a vacuumed plunger that retracts the needle into a piston cavity. Also, U.S. Pat. No. 5,045,062 to Henson discloses a fluid turbine propelled by the syringe flow to interlock the plunger and barrel. U.S. Pat. No. 5,190,526 discloses a needle carriage assembly detachably fastened to the inside of the nozzle of the barrel by four catches while the plunger is provided with a coaxial cavity containing a spring-loaded mating member corresponding to a mating member extending from the needle carriage. At the end of the advancement of the plunger the mating mechanism is actuated and the needle carriage is pulled inside the cavity of the plunger.

Various drawbacks are associated with the above approach. One drawback is that normal reciprocal movement of the plunger to withdraw blood and inject medicines is itself used to actuate coupling of the needle and the plunger and to cause retraction of the needle. That is, the normal functional action of moving the plunger coincides with the coupling, retracting, and locking action of the needle. This makes these syringes unreliable and decreases their functionality. Moreover, the mechanics of these syringes are complex and the results are unpredictable. Since many of these syringes require the plunger to be pulled outward in order to lodge the needle in the barrel of the syringe, such syringes tend to be bulky following use because of their increased size with the plunger pulled outward. This, in turn, adds volume to disposed syringes.

Venipuncture of superficial thin-walled veins that often slip during the puncture is a precision technique. It is essential that the insertion force is at an accurate point and is just enough to puncture the vein. The blood-tinged needle also needs to be totally enclosed. This demands a stable hypodermic needle assembly that functions as a single entity and delivers puncturing force at a precise point at an appropriate angle and in an accurate amount. The prior art does not satisfy all these requirements.

Second, with respect to guidewire insertion, a guidewire is placed in a central vein through an in-line valve following percutaneous venipuncture with a hypodermic needle. Examples of guidewire inserters and devices which can be used as guidewire inserters are described in U.S. Pat. Nos. 4,233,982; 4,274,408; 4,424,833; 4,468,224; 4,529,399; 4,813,938; and 4,898,588. Other examples are described in German Patent Nos. 2415196, 2507119, and 3042229, and French Patent No. 2.004.771. In the brief descriptions of these patents which follow, the numerals in brackets refer to reference numerals used in the drawings of the patents.

U.S. Pat. No. 4,233,982 to Bauer et al. describes a trocar sleeve [2] with an in-line connector that incorporates a U-shaped insert [7] and a ball [10] which is retained in concavity of "U" by a spring mechanism [11] and acts as a valve. When a trocar is inserted through the sleeve [2], the valve opens to provide a flow path.

U.S. Pat. Nos. 4,245,635 and 4,261,357 to Kontos disclose catheters for intermittent intravenous use. In each of the Kontos patents, a needle [14] is inserted for OTN placement of an elastomeric catheter [10]. In U.S. Pat. No. 4,245,635, the hub [19] of the catheter [10] contains a ball valve with a ball [26] and an arm [28] attached to the ball [26]. The arm [28] extends through an aperture [24] in a fixed insert [22] within the hub [19] and has a right angled tab [29] which lies parallel to the insert [22]. After inserting the catheter [10] over the needle [14] and withdrawing the needle [14], backflow of blood is prevented by the valve. Insertion of a syringe or any male luer [32] pushes the ball [26] away and permits the infusion of the fluids. U.S. Pat. No. 4,261,357 shows a penetrable and self-sealing membrane [22] attached to the proximal end of an elastomeric catheter [10]. The membrane [22] prevents the backflow of blood while fluids are given to a patient by a needle [14] inserted in the membrane [22].

U.S. Pat. No. 4,274,408 to Nimrod describes a thin feeder tube [18] located in the central passage of a plunger [20] with a ball valve [42] at the end of the plunger [20]. Advancement of the feeder tube [18] displaces the ball [42] and communicates the passage with the lumen of a needle [30], thereby permitting a guidewire [12] to be fed into the vein.

U.S. Pat. No. 4,424,833 to Spector et al. describes a one-piece molded self-sealing gasket [14] including an outer sealing portion [42] with a central circular hole [48] and inner seal [44] provided with slits [50] defining a plurality of resilient flaps [52]. When a catheter [51] is inserted, it seals an aperture [48] and deflects the flaps [52]. When the catheter [51] is removed, the resilient flaps [52] seal the gasket. The gasket [14] will remain closed despite fluid removal through the side nozzle [18].

U.S. Pat. No. 4,529,399 to Ghorshong et al. describes a method for percutaneous insertion of a closed ended catheter [20] through the bore of the needle [16]. The catheter [20]

is disposed within the needle [16]. One end of a stainless steel internal pushing stylus [22] is inserted in the catheter [20] while other end is attached to a plunger [14] of a syringe [12] containing fluid. A coupler [48] is attached to the plunger end and holds the catheter [20]. The distal end of the stylus [22] has a cross element [54] before it passes through the coupler [48]. After puncture by the needle [16], advancement of the plunger [14] pushes the fluid to dilate the vein as well as advance the catheter [20] via the stylus [22].

U.S. Pat. No. 4,813,938 to Raulerson describes a catheter introduction syringe [10] having a barrel [12] with a hollow tip [18] and a plunger [14]. The plunger [14] comprises two substantially cylindrical elements [22, 24] and a valve recess [26] for each of them. The first element [22] contains a cylindrical body [30] with a central channel [32] and a plunger seal [36]. The second element [24] continues from the first element [22] and contains a central channel [48] and a counter sunk recess [40]. A valve assembly [28] is located between the elements [22, 24] and includes first and second one-way valve elements [58, 59] which form a valve chamber [60] therebetween. The valve elements [58, 59] comprise flexible resilient hollow, substantially hemispheric members [62] having an annular flange [62]. A normally closed centrally disposed slit or aperture [66] is formed in the center of each hemisphere. A rigid valve support [68] is provided in the center of the resilient valve assembly [28]. For use the syringe [10] functions as an ordinary syringe. During aspiration, fluid enters the barrel [12] of the syringe [10] while air is prevented from entering the valve chamber [60] by the second valve element [59]. Once aspirated, the blood may be flushed from the syringe [10]. While flushing, a first valve element [58] prevents liquid from passing through the centrally disposed channel [32] into the valve chamber [60]. A guidewire or catheter may then be passed through the syringe [10] into the blood vessel through the slit valves without any transport of fluid or air. A drawback of the syringe in Raulerson is that the syringe may cause air embolism because the syringe pushes air before the fluid.

U.S. Pat. No. 4,842,591 to Luther describes a one-way deformable slit septum valve [33] in a connector for maintaining sterility and for preventing the backward flow of blood and body fluids through the connector. A movable hollow plug [35] is adapted to deform and enter the septum slit [34] and maintain the slit [34] open when pushed by a syringe nozzle or intravenous luer. When the nozzle is withdrawn, resilience of the septum [33] pushes the plug [35] back out of the septum [33] and closes the slit [34]. Although intended for fluid infusions, the connector in the Luther patent can be used for guidewire insertion.

U.S. Pat. No. 4,898,588 provides a guard to prevent jets or streams of blood from spurting through the guidewire introducer needle following percutaneous venipuncture. Furthermore, U.S. Pat. No. 4,468,224 to Enzmann et al. describes multiple co-axial hypodermic needles for inserting a guidewire for placement of a catheter with multiple connectors and valves.

German Patent No. 2415196 describes a syringe with an eccentric nozzle and an eccentric valve located in the plunger. A guidewire is passed through the plunger head, through the valve, through the nozzle, through a needle, and finally into the vein. German Patent No. 2507119 shows a guidewire attached to a plunger head and a central channel passing through the plunger communicating with a needle. Another German Patent No. 3042229 discloses a valve arrangement in the plunger head possibly for guidewire insertion. A French patent 2.004.771 describes a single lumen catheter with a two way Y connector.

Once again, a major problem associated with guidewire inserters (besides blood sputtering and air embolism) is the possibility of accidental needle puncture following use of the needle. None of the above patents addresses this problem.

Third, with respect to collecting blood samples using a double pointed hypodermic needle, approaches to protecting against needle punctures have been directed toward needle caps, safety disposal containers, and protective sleeves. Examples of such needle protection devices are described in U.S. Pat. Nos. 4,731,059; 4,782,841; 4,813,426; 4,819,659; 4,887,998; 4,927,019; 5,000,167; 5,002,536; 5,030,209; 5,069,669; 5,181,524; and 5,188,119. U.S. Pat. No. 4,731,059 to Wanderer describes a two-piece protective shield [FIG. 6] to enclose the double ended needle for maintaining sterility and preventing accidental needle sticks. Also described is a slidable co-axial sleeve on a venipuncture needle (See FIGS. 20 and 21).

U.S. Pat. No. 4,782,841 to Lopez discloses a venipuncture needle having a guard assembly consisting of a collar [80] and co-axially slidable and lockable guard [70]. In a first position the venipuncture needle is exposed, while in a second position the guard is advanced and locked so as to conceal the venipuncture needle.

U.S. Pat. No. 4,819,426 to Haber discloses a shielded safety syringe [1] comprising an outer protective sleeve [2] having an open proximal end, a substantially closed distal end except for a central opening [6] to accommodate the distal venipuncture [44] end of the double ended needle, an inner spring biased cylindrical needle carrier [14] with open proximal end and closed distal end except for a central opening to accommodate the vaccutainer end covered by the protective sheath [18] of the double ended needle. Coaxially aligned with the needle carrier is a double ended hypodermic needle [8]. Extending radially from opposite side of the needle carrier [14] are a position control button [20] and guide tab [22], adapted to be received in and slid through the axial guide channels [9] and [10] locked with detentes [12] and [13] of the outer sleeve [2]. A helical compression spring [30] is received within the outer sleeve [2] and needle carrier [14]. The reciprocating action of the sleeve [2] and needle carrier [14] permits a change in the axial length of the sleeve and the needle carrier. Advancing the sleeve conceals the venipuncture end of the needle. This action is aided by the spring but same can be done manually without a compression spring [30].

U.S. Pat. No. 4,819,659 to Sitar describes a unitary structure [14] consisting of tube holding section [16] and locking section [18]. The needle guard [20] is located co-axially on the tube forming locking section [18] and lockably encloses the needle. Advancing the sheath forward encloses the entire venipuncture needle section.

U.S. Pat. No. 4,887,998 to Martin discloses a tapering plastic cap [33] with an apical opening [39] and a compressed co-axial spring [27] is located at the base of a venipuncture needle [19]. The needle projects through the opening [39]. After using the needle, the latch [29] is released, recoiling the spring [27] and advancing the cap beyond the tip of the needle. The end of the needle abuts against a ball [37] and is prevented from protruding through the end hole [39].

U.S. Pat. No. 4,927,019 to Haber et al. describes a sterile packaging for a double ended blood collection needle to solve the problem of needle sticks which occur during attachment of the needle to the barrel. Haber et al. does not address the issue of contaminated needle pricks caused by the puncturing needle. Disclosed is a needle sheath and sterility package comprising a lower needle cover [2] to surround and protect the distal end of a double ended hypodermic cannula [6] and an upper sleeve [4] to surround and protect the proximal end [8] of the cannula. The upper sleeve can be opened to permit the bore of the conventional hypodermic syringe to be received.

U.S. Pat. Nos. 5,000,167 and 5,188,119 to Sunderland describe a blood collection device [10] having a foldable one-piece molded housing [16 and FIG. 4A] enclosing a non-linear needle [24] with parallel ends [38 and 34] projecting in opposite directions proximally and distally. The distal end [38] is enclosed in a plastic tubular protective sheath [28] that is mounted on a shield assembly [27]. The shield assembly is capable of reciprocal sliding action by displacing the finger assembly [30]. A slot [40] on the tubular needle protective shield [28] permits retraction of the shield [28] at the angular portion of the needle. The protective shield is lockable at two positions [46 and 52]. A rectangular hard case [56] encloses the proximal compartment while another tubular hard case [60] encloses, protects and maintains sterility of the distal needle and protective shield. Another similar embodiment is also described.

U.S. Pat. No. 5,002,536 to Thompson describes a conventional needle protector that has an inside diameter [36] smaller than the outside diameter [26] of the needle hub. Inside the protector are projections [44] which lock with the projections on the needle hub [22]. The protector includes a wide conical mouth to prevent injury to fingers during the insertion of the needle inside the needle protector.

U.S. Pat. No. 5,030,209 to Wanderer et al. describes a double ended needle mounted on a syringe slideably connected to a coaxial tube. Advancement or retraction of the co-axial tube conceals the projecting end of the double ended needle. The holder includes an insert [12] for supporting the double ended needle. The insert has a tab which enters and slides into a slot located on a sleeve [50] of cylinder [14]. The cylinder is co-axially located on the insert, which is freely movable and lockable at two positions within the cylinder. Locking is achieved by engaging tabs on the insert with the slots on the cylinder. Forward movement of the sleeve [50] shields the venipuncture needle. Other capping and sleeving mechanisms are also described.

U.S. Pat. No. 5,069,669 to Kole discloses a finger guard [25] including a tubular element [26] of flexible needle puncture resistant material. The tubular element [26] has first [27] and second [28] circumferentially contiguous end sections joined by a plurality of longitudinally expanding circumferentially contiguous stripes [29] which project radially to form an umbrella like structure and protect against needle sticks when expanded.

U.S. Pat. No. 5,181,524 to Wanderer et al. discloses an extension of the interconnection between a double ended needle and a needle holder [FIGS. 38–46] which permits a large girth holder to be employed without compromising the preferred needle entry angle. Other embodiments of the needle guard include telescoping guards [FIGS. 38 and 46] to shield the lengthy needles. Each guard is manipulated from the rear. An annular trough within the needle guard restrains the flow of contaminated liquids.

These devices suffer from the drawbacks described above. In particular, needle caps and safety disposal containers do not provide adequate safety against needle punctures. Also, the devices which include protective sleeves are bulky, interfere with a person's grip and transmission of insertion force, disturb the insertion angle of the needle for penetration into the vein, and have the problem of sleeve dislodgement. Finally, coaxially-advancing needle protective devices have one or more of the previously discussed drawbacks, i.e., reduced functionality, unreliability, complexity of design, and-high cost.

Fourth, metallic hypodermic needles attached to a fluid line are primarily used for infusing intravenous fluids. In addition, these hypodermic needles are used for taking medication out of vials, mixing the medication, and transferring it to intravenous bags. Although such handling of hypodermic needles may cause accidental needle pricks, the needles are not infected until a vein of a patient is punctured by the needles. Various attachments designed to protect against needle pricks mount on the sharp tip of needles. Examples of such attachments are described in U.S. Pat. Nos. 3,610,240; 3,658,061; 4,735,618; 4,747,836; 4,838, 871; 4,846,811; 4,874,384; 4,929,241; 4,944,728; 4,944, 731; 5,030,212; 5,037,400; 5,037,401; 5,049,136; 5,053, 017; 5,059,180; 5,067,944; 5,067,946; 5,078,693; 5,116, 325; 5,135,504; 5,171,303; 5,176,655; 5,183,468; and 5,188,611. The foregoing bare hypodermic needles have to some extent been replaced by OTN catheters made of flexible plastic elastomers which minimize trauma to veins. Even though the OTN catheters protect the interior of veins from mechanical trauma, hypodermic needles used to introduce such OTN catheters still present a major problem due to the high volume of intravenous fusion procedures. Examples of OTN catheters are described in U.S. Pat. Nos. 4,245,635; 4,261,357; 4,747,831; 4,762,516; 4,828,548; 4,832,696; 4,850,961; 4,950,252; and 4,964,854.

U.S. Pat. No. 4,747,831 to Kulli discloses an OTN catheter provided with a hollow handle [10] having a needle-carrying block [30] within the handle, a nose piece [20] fixed to the front of the handle, and a latch [40] that holds the block [30] in a forward position within the handle. The block [30] extends through the handle [10], and the handle [10] has a grip surface [11] and thumb stop [15]. The anterior surface of the thumb stop is slotted to form two latch guides [16 and 18]. A centered longitudinal bore [12] is formed in the handle [10] and bottom surface of the latch guide slot. The nose piece [20] is a circular plate [22] with a nozzle [21]. The latch [40] is made from stainless steel having a fiat slide section [41] and a push button section [42].

U.S. Pat. No. 4,828,548 to Walter describes a safety catheter [30] including a plastic cannula [14] with a hub [15], and a mounted rubber seal [38] with an opening [38a] located in a counter sunk recess [52] having a channel [44] in the end wall [45] of the housing [32]. The catheter is located on a needle [34] that communicates with a flashback chamber [36] attached to a rubber piston [42]. The housing [32] is made of clear plastic and contains a vacuum. The seal [38] resists the movement of piston [42]. When the catheter [14] is placed in the vein, the hub [15] and seal [38] are separated from the housing [32]. Piston [42] retracts so as to conceal the needle. In another embodiment, a spring [62] mounted between piston [64] and end wall [66] may be utilized to drive the piston [64] back.

U.S. Pat. No. 4,832,696 to Luther discloses a clear plastic housing [11] with a magnifying portion [13] having a rear mount [14] with an extension [14a] adapted for securing a syringe [28]. The exterior surface of the housing has grip ridges [16], and the front end [15] of the housing [11] is open for sliding forward a needle guard [23]. The inner surface of the front end has a detente locking slot [18] that engages tabs [25] at the end of the needle guard. The outer edge of the housing has stop wings [17]. A needle [22] is secured to the end [14a] of the housing [11]. The needle guard [23] is slidably mounted in the housing [11] and carries a forwardly located pull tab [24] and outwardly bent locking ears [25]. A forward hub support [26] is provided by the needle guard through which the needle [22] projects out. The combined effect of fixed rear mounting [14 and 4a] and hub support [26] enables the needle to be rigidly maintained in alignment. A catheter [31] with hub [30] is mounted on hub support [26]. A cover [32] to protect the needle tip [22a] is secured by a light interlock with wings [17] of housing [11]. As shown in FIG. 9, after the OTN catheter is inserted, the needle can be withdrawn by pressing against forward tab [24] while retracting the housing [11] and the attached needle [22], until the locking ears [25] of needle guard [11] lock in detente slots [18]. The syringe support [26] is disengaged and discarded. Other embodiments are shown in FIGS. 5–6 and FIGS. 7–8.

U.S. Pat. No. 4,850,961 to Wanderer describes an indwelling catheter placement enclosed in a removable shield [14] engaged and taped to an end cap [12] which is fixed to the end of a rigid tubular guard [20]. The guard has grip areas [24] on the sides while the anterior end has a needle passage aperture [26]. A longitudinal slot [30] permits the reciprocal movement of a tab [32] that is attached to the needle assembly. After usage, the shield is removed and the tab [32] is pushed anteriorly. This action advances the needle assembly [40] and the catheter assembly [42]. Once the catheter is inserted in a vein, the tab [32] is pulled back along the slot [30]. The hub of the needle [46] contains a semipermeable valve for venting and a flashback prevention valve. The assembly is intended to be transparent.

U.S. Pat. No. 4,950,252 to Luther et al. discloses a catheter assembly [10] having a housing block [12] that encloses a needle mount [28] formed by housing block [12] with a channel [26] to enclose a needle guard [14] for linear movement. The distal end of the needle guard [14] is provided with hub mount [32] and an actuator tab [36] on the upper exterior surface above the level of the housing block [12]. The opposite ends of the needle guard [14] have locking ears [38] that lock on the locking slots [30] of the housing block [12] when retracted. A medical needle [16] secured to the housing block projects through the hub mount [32] of the needle guard [14] and passes through the catheter hub [20] lumen [18] and projects as sharp end [16a]. For operation the OTN catheter is inserted in the vein. Keeping the tab [36] steady with one finger, the housing block is retracted backwards on the protector until the locking ears [38] of the protector engage with locking slots [30] of the housing block. The needle is now withdrawn and secured.

Existing OTN catheters suffer from penetration problems because of long length needles and unsecured needle supports. In addition, existing OTN catheters still present the danger of causing needle pricks due to ineffective encasement of the needles following use.

Accordingly, there exists a need for a hypodermic needle assembly which overcomes the above-noted drawbacks associated with existing assemblies.

SUMMARY OF THE INVENTION

A primary object of the present invention to provide a hypodermic needle assembly which perform all the conventional functions of the hypodermic needle, and yet allows the hypodermic needle to be retracted and concealed in a barrel or chamber of the assembly following use.

Another object of the present invention is to provide a hypodermic needle assembly which includes a securely attached hypodermic needle and which promotes easy puncture of patient's skin and veins, and yet allows the hypodermic needle to be retracted and concealed in a barrel or chamber of the assembly in response to actuation of a retracting mechanism.

Yet another object of the present invention is to provide a hypodermic needle assembly which avoids inadvertent activation and premature retraction of the needle before or during the use of the assembly. A related object of the present invention is to provide a hypodermic needle assembly which can be used any number of times without the needle automatically and inadvertently retracting into a barrel or chamber following a single use.

Still another object of the present invention is to provide a hypodermic needle assembly which irretrievably locks and immobilizes a retracted needle inside the barrel or chamber such that the retracted needle cannot be removed from the barrel unless it is intentionally broken and destroyed. Thus, the assembly is irreversibly safe.

Another object of the present invention is to provide a hypodermic needle assembly which permits the hypodermic needle to be retracted and concealed in a barrel or chamber of the assembly without the user positioning his or her fingers near the sharp point of the hypodermic needle.

A further object of the present invention is to provide a hypodermic needle assembly which is cost-effective and easy to manufacture.

Yet a further object of the present invention is to provide a hypodermic needle assembly which is easily used by persons for legitimate self-care purposes, such as for management of diabetes, asthma, migraines, etc.

In accordance with the present invention, the foregoing objectives are realized by providing a needle-syringe assembly, operable in a normal mode and convertible to a retraction mode, comprising an elongated, generally cylindrical barrel forming a hollow nozzle located at the distal end of the barrel and opening into the interior of the barrel; a plunger slidably mounted in the barrel and forming a coaxial cavity extending between the distal end and the proximal end of the plunger; a needle holder carrying a hollow needle on the distal end thereof, the needle holder being slidably mounted in the coaxial cavity of the plunger, the needle holder being detachably engaged to the barrel with the distal portion of the needle holder being disposed within the nozzle of the barrel during the normal mode; and a coupling mechanism, responsive to rotation of the plunger relative to the barrel, for disengaging the needle holder from the barrel to switch the assembly from the normal mode to the retraction mode and for retracting the needle holder into the coaxial cavity of the plunger such that the needle is concealed within the barrel and is substantially concealed within the plunger.

In addition, the present invention provides a guidewire insertion assembly comprising the foregoing elements of the needle-syringe assembly. The guidewire insertion assembly further includes a one-way valve disposed within the needle holder for permitting a guidewire to pass therethrough in one direction and for preventing blood from passing therethrough in the opposite direction. Also, the needle holder is hollow with openings at both the distal and proximal ends of the needle holder to permit a guidewire to pass through the needle holder.

Furthermore, the present invention provides a blood sample collection assembly operable in a normal mode and convertible to a retraction mode, comprising a first chamber forming a hollow nozzle located at the distal end of said first chamber and opening into the interior of said first chamber; a second chamber adjacent to said first chamber; a vacuum tube chamber connected to said first chamber and positioned substantially orthogonal to said first chamber, said vacuum tube chamber having an open end for receiving a vacuum tube; a needle carrier carrying a first hollow needle on the distal end thereof and carrying a second hollow needle substantially orthogonal to said first hollow needle, said second hollow needle being in fluid communication with said first hollow needle, said second hollow needle extending into said vacuum tube chamber, said needle carrier being slidably mounted in said first chamber, said needle carrier being detachably engaged to said first chamber with the distal portion of said needle carrier being disposed within said nozzle of said first chamber during the normal mode; and a retraction means for disengaging said needle carrier from said first chamber to switch the assembly from the normal mode to the retraction mode and for retracting said needle carrier into the first chamber such that said first needle is concealed within said first chamber and said second needle is concealed within said second chamber.

The present invention further provides an over-the-needle catheter assembly, operable in a normal mode and convertible to a retraction mode, comprising an elongated, generally cylindrical needle chamber forming a hollow nozzle located at the distal end of the needle chamber and opening into the interior of the needle chamber, the needle chamber having a longitudinal slot formed in the cylindrical wall of the needle chamber; a needle carrier slidably mounted within the needle chamber for movement between a forward position and a retracted position, the needle carrier having a hollow needle mounted thereon, the needle protruding through the nozzle when the needle carrier is in the forward position, the needle being concealed by the needle chamber when the needle carrier is in the retracted position; a latch mechanism, coupled to the needle carrier through the longitudinal slot, for engaging the needle carrier in the forward position during the normal mode and for disengaging the needle carrier to initiate the retraction mode; and a locking mechanism for locking the needle carrier in the retracted position.

BRIEF DESCRIPTION OF THE DRAWINGS

Other objects and advantages of the invention will become apparent upon reading the following detailed description and upon reference to the drawings in which:

FIG. 7a is a fragmentary perspective view of the needle-syringe assembly showing a flag-shaped clamp retaining the lateral arm of the needle holder within the oblique slot;

FIG. 7b is a fragmentary perspective view of the needle-syringe assembly showing the flag-shaped clamp in a rotated position for releasing the lateral arm from the oblique slot;

FIG. 15 is a longitudinal section of the guidewire insertion assembly in FIG. 14 with the needle inserted into a vein of a patient;

FIG. 16 is a longitudinal section of the guidewire insertion assembly in FIG. 14 with a guidewire inserted through the assembly into a vein of a patient;

FIG. 17 is a longitudinal section of the guidewire insertion assembly in FIG. 14 with a guidewire inserted into a vein of a patient, the needle carrier in the retracted position, and the needle concealed by the needle chamber;

FIG. 21a is a side plan view, taken orthogonal to the longitudinal sections in FIGS. 18–20, of the blood sample collection assembly embodying the present invention;

FIG. 21b is a top plan view of the blood sample collection assembly in FIG. 18;

FIG. 21c is a longitudinal section of the blood sample collection assembly in FIG. 18 with the needle carrier and mounted needles being shown in the forward position (solid lines) and the retracted position (dotted lines);

FIG. 23b is a perspective view showing the manner of assembly of the blood sample collection assembly in FIG. 23a;

FIG. 24 is an enlarged cross-section of an over-the-needle catheter assembly embodying the present invention;

FIG. 25 is a section taken generally along line 25—25 in FIG. 24;

FIG. 27 is a perspective view of a T-latch for retracting the needle carrier of the over-the-needle catheter assembly with the T-latch shown in the forward position;

FIG. 28 is a fragmentary section taken generally along line 28—28 in FIG. 27; and FIG. 29 is a perspective view of a T-latch for retracting the needle carrier of the over-the-needle catheter assembly with the T-latch shown in the retracted position.

Figure 1:
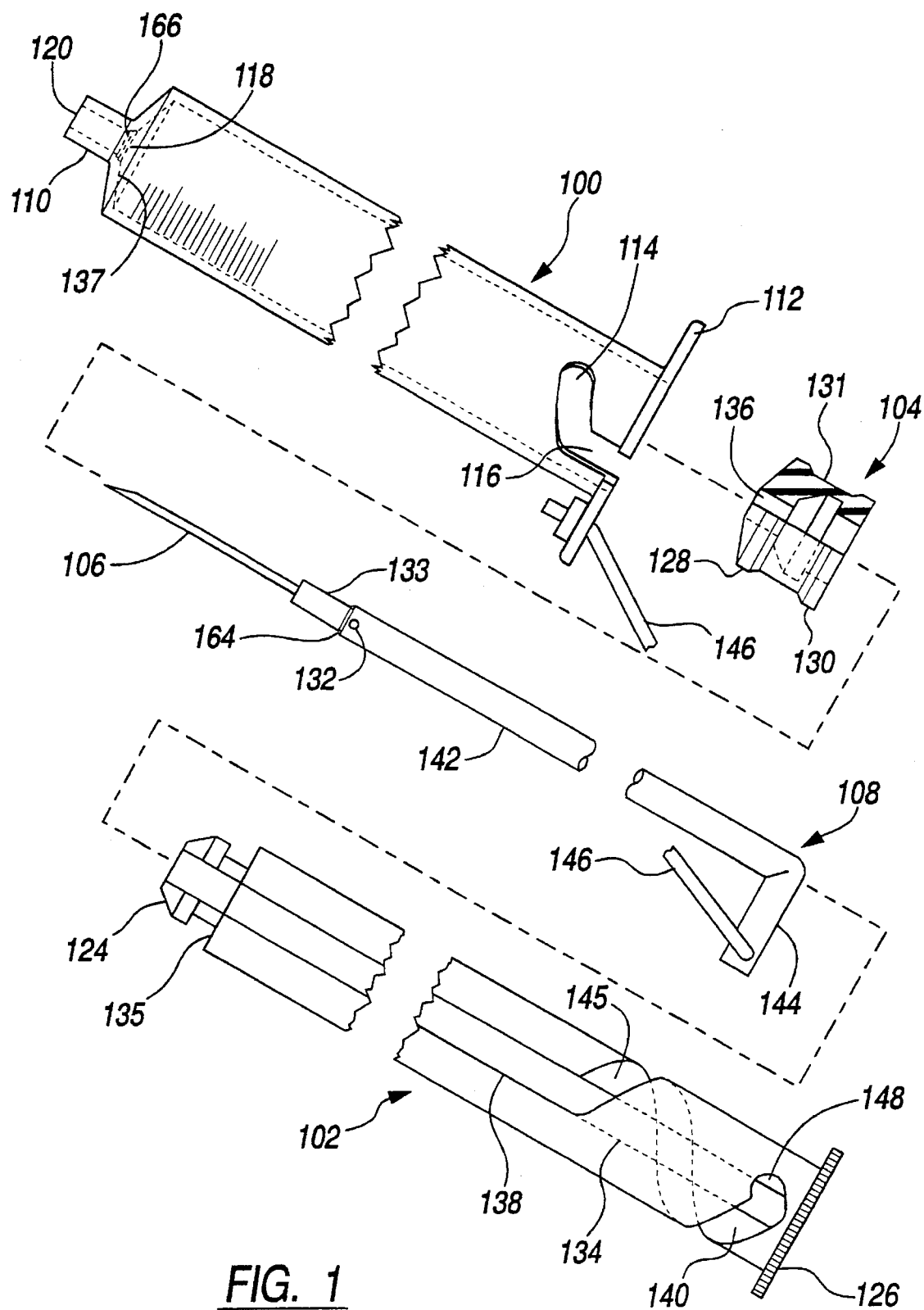
FIG. 1 is an exploded plan view of a needle-syringe assembly embodying the present invention.

While the invention is susceptible to various modifications and alternative forms, a specific embodiment thereof has been shown by way of example in the drawings and will herein be described in detail. It should be understood, however, that it is not intended to limit the invention to the particular forms disclosed, but on the contrary, the intention is to cover all modifications, equivalents, and alternatives falling within the spirit and scope of the invention as defined by the appended claims.

DESCRIPTION OF THE PREFERRED EMBODIMENTS

Turning now to the drawings, FIGS. 1–12 illustrate a needle-syringe assembly including a barrel 100, a cylindrical plunger 102, a hollow plunger cap 104, a hypodermic needle 106, and a needle holder 108. The barrel 100 is a hollow tube with a hollow tapered conical nozzle 110 at the distal end thereof. The interior of the conical nozzle 110 communicates with the hollow tube of the barrel 100. The proximal end of the barrel 100 is provided with a transverse circular base plate 112 employed to pull or push the plunger 102 in relation to the barrel 100. The barrel 100 contains an oblique retainer slot 114 and a longitudinal travel slot 116 connected thereto. The longitudinal travel slot 116 extends through the base plate 112 at the proximal end of the barrel 100. The outer surface of the barrel 100 preferably contains graduations indicating the volume level of fluid in the barrel 100. These graduations take into account the volume of the needle holder 108. In the preferred embodiment, the inner diameter at the junction 118 of the nozzle 110 and barrel 100 is 0.120 inches while the inner diameter at the distal end 120 of the nozzle 110 is 0.110 inches. Moreover, the longitudinal distance between these two inner diameters is 0.250 inches. The diametric difference between the two diameters forms a taper in the nozzle 110 which is conventionally known as a locking female luer taper, and the angle formed by the diametric difference is conventionally known as a locking taper angle.

The elongated plunger 102 includes a head 124 to accommodate the hollow rubber plunger cap 104, and a base plate 126 grasped by a user to permit linear or rotary movement of the plunger 102 relative to the barrel 100. The surface of the base plate 126 is provided with longitudinal grooves to facilitate gripping of the base plate 126 for rotary movements of the plunger 102. The outer diameters of the ends 128, 130 of the resilient plunger cap 104 are wider than the outer diameter of the central cylindrical portion 131 of the cap 104. Furthermore, the outer diameters of the ends 128, 130 of the cap 104 are slightly larger than the inner diameter of the barrel 100 so that an air-tight and liquid-tight seal is formed between the plunger cap 104 and the inner surface of the barrel 100. The distal end 128 of the cap 104 is conical and abuts the complementary distal end of the barrel 100 when the plunger 102 is advanced inside the barrel 100.

The head 124 of the plunger 102 is configured to fit tightly within the hollow plunger cap 104. With the cap 104 locked over the head 124 of the plunger 102, the flat proximal end 130 of the cap 104 abuts the flat surface 135 of the plunger 102. Due to the air-tight and liquid-tight seal between the plunger cap 104 and the barrel 100, forward axial movement of the plunger 102 inside the barrel 100 creates pressure in the barrel interior between the distal end 128 of the plunger cap 104 and the distal end of the barrel 100. Similarly, backward axial movement of the plunger, i.e., pulling out the plunger, creates a vacuum in that barrel interior. In an alternative embodiment, the resilient cap 104 is substituted with a resilient "O" ring at the flat end of the plunger 102.

The hypodermic needle 106 is mounted on the distal end of the elongated cylindrical needle holder 108, which is detachably interlocked to the barrel 100 by the taper lock between the distal cylindrical portion 133 of the needle holder 108 and the inner surface of the nozzle 110. To aid in securing the distal cylindrical portion 133 of the needle holder 108 within the nozzle 110 and to create an air-tight and liquid-tight seal between the needle holder 108 and the inner surface of the nozzle 110, the mating surfaces of the nozzle 110 and the needle holder 108 are textured. The tight contact provided by the textured surfaces also functions to minimize leakage of barrel contents through the nozzle 110 while injecting fluids. To further minimize leakage, the needle holder 208 is provided with an elastomeric or rubber "O" ring 164 at the proximal end of the cylindrical portion 133. The "O" ring 164 mates with circular groove 166 formed in the inner surface of the nozzle 210. The "O" ring 164 and the groove 166 strengthen the contact between the mating surfaces of the nozzle 110 and the needle holder 108. In addition, the apex 137 of the barrel 100 may also be inverted (not shown) such that the angle of the apex 137 is sloped toward the proximal end of the barrel 100 rather than away from the proximal end of the barrel 100. With such a barrel apex, leakage of barrel contents is further minimized by providing the needle holder 108 with a mating inverted portion.

Figure 3:
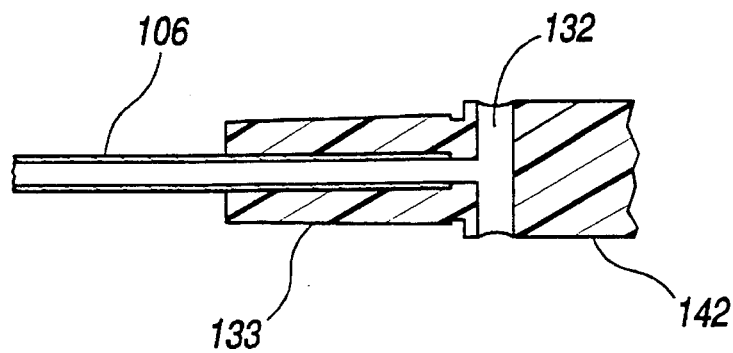
FIG. 3 is a fragmentary longitudinal section through a distal portion of the needle holder of the needle-syringe assembly in FIG. 1.

Prior to using the needle-syringe assembly, the needle 106 is covered by a protective cap (not shown) which prevents needle pricks and preserves sterility prior to use. Both the needle 106 and the distal portion of the needle holder 108 are hollow, and the interior of the hollow needle 106 communicates with the interior of the hollow distal portion of the needle holder 108. The needle holder 108 further communicates with the interior of the barrel 100 by a transverse channel 132 which intersects the interior of the needle holder 108 (FIG. 3). Prior to and during use of the needle-syringe assembly for injection of medicine or withdrawal of blood (hereafter referred to as "normal use"), the transverse channel 132 is positioned at the apex 137 of the barrel 100. The transverse channel 132 permits blood or medicine to enter or exit from the barrel 100 via the needle holder 108 and the needle 106. The distal cylindrical portion 133 of the needle holder 108 is sized to fit tightly within the nozzle 110 of the barrel 100 to form the disengagable taper lock. The taper lock is formed by axially telescoping identical diameters. In particular, the cylindrical portion 133 of the needle holder 108 has outer diametric dimensions equivalent to the inner diametric dimensions of the nozzle 110. Thus, the distal end of the cylindrical portion 133 has an outer diameter of 0.110 inches while the proximal end of the cylindrical portion 133, which is positioned adjacent to the junction 118 between the nozzle 110 and the barrel 100, has an outer diameter of 0.120 inches.

The plunger 102 contains a coaxial cavity 134 extending from the head 124 to the base plate 126. The coaxial cavity 134 is diametrically sized to accommodate the needle holder 108 and to permit reciprocating axial relative movement between the needle holder 108 and the plunger 102. Moreover, the distal portion 128 of the plunger cap 104 contains a tight axial cavity 136 sized to accommodate the needle holder 108 and, at the same time, to prevent air or liquid leakage through the cap 104. If a resilient "O" ring is used in place of the plunger cap 104, another "O" ring is placed in the coaxial cavity 134 to surround and seal the needle holder 108.

The coaxial cavity 134 is exposed to the outer surface of the plunger 102 by a longitudinal slot 138 and a helical slot 140. The longitudinal slot 138 extends from the distal end of the plunger cap 104 to the distal end of the helical slot 140. The longitudinal slot 138 leads into the helical slot 140, which extends between the proximal end of the longitudinal slot 138 to a longitudinal position spaced from the base plate 126. The functions of these two slots 138, 140 are discussed below.

Figure 6A:
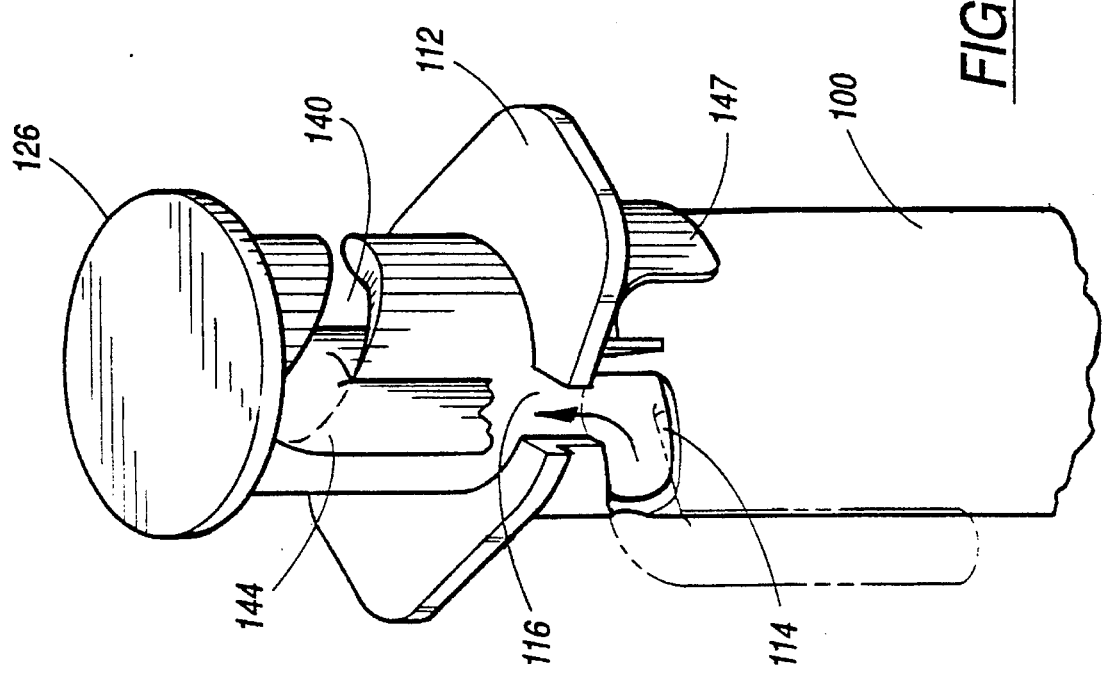
FIG. 6a is a fragmentary perspective view of the needle-syringe assembly showing a C-clamp retaining the lateral arm of the needle holder within the oblique slot.
Figure 6B:
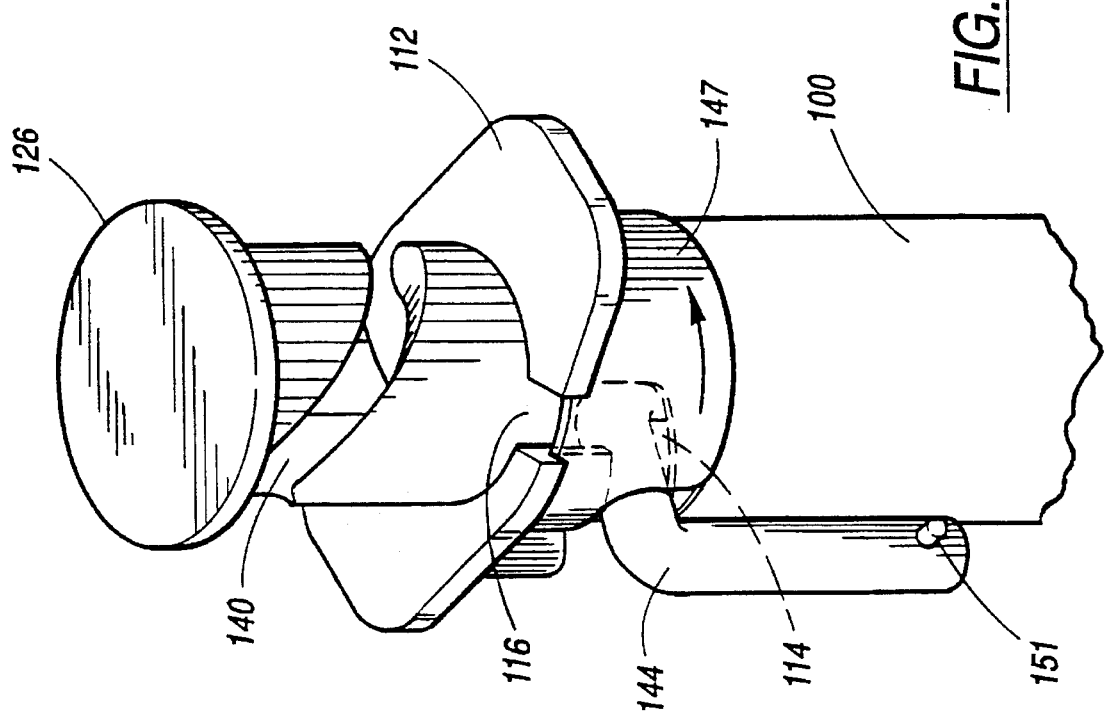
FIG. 6b is a fragmentary perspective view of the needle-syringe assembly showing the C-clamp in a rotated position for releasing the lateral arm from the oblique slot.

During normal use of the needle-syringe assembly, the distal cylindrical portion 133 of the needle holder 108 is locked within the nozzle 110 of the barrel 100, and the needle holder 108 is slidably mounted within the coaxial cavity 134 of the plunger 102 as well as the coaxial cavity 136 of the plunger cap 104 (FIGS. 2, 5, 10, and 11). The needle holder 108 is L-shaped, having a leg portion 142 and a lateral arm 144 oriented ninety degrees from the leg portion 142. With respect to the barrel 100, the leg portion 142 of the L-shaped holder 108 extends coaxially from the nozzle 110 to the oblique slot 114, and the lateral arm 144 extends transversely through the distal portion of the oblique slot 114 (via the longitudinal slot 138 in the plunger 102). The lateral arm 144 is maintained within the distal portion of the oblique slot 114 by a C-clamp 147 anchored in a groove in the outer surface of the barrel 100 (FIGS. 6a and 6b). The C-clamp 147 is snugly positioned between the base plate 112 of the barrel 100 and the lateral arm 144, biasing the lateral arm 144 into the distal portion of the oblique slot 114 during normal use of the assembly. Alternatively, a flag-shaped clamp 149 may be rotatably hinged to an L-shaped lateral arm 144a (FIGS. 7a and 7b). The flag-shaped clamp 146 is positioned between the lateral arm 144a and the base plate 112 to maintain the lateral arm 144a within the oblique slot 114, and is rotated from beneath the base plate 112 to permit movement of the lateral arm 144a out of the oblique slot 114.

Figures 10, 11, 12:
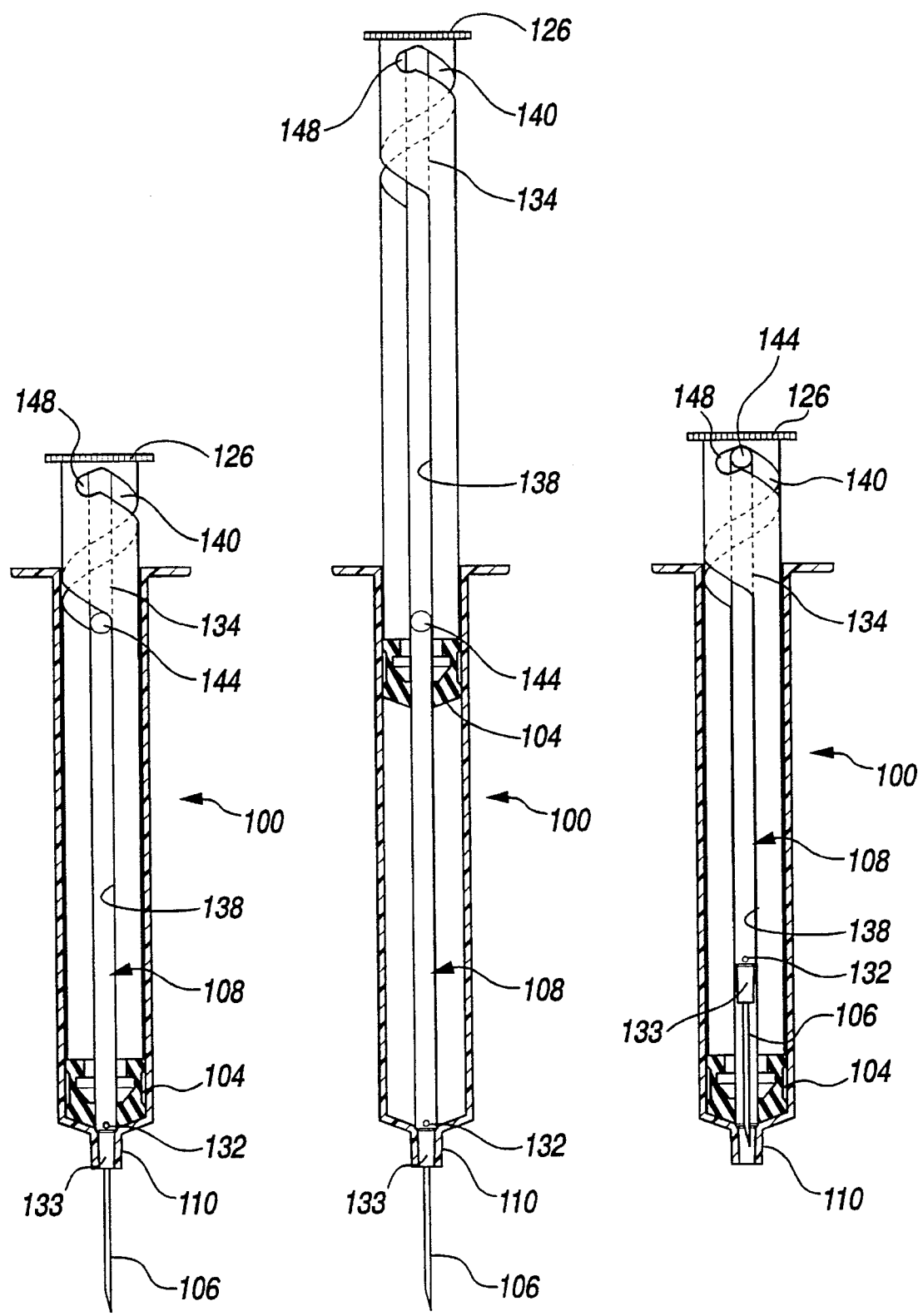
FIGS. 10 and 11 are longitudinal sections of the needle-syringe assembly in FIG. 2 showing the available range of axial movement of the plunger relative to the barrel.
FIG. 12 is a longitudinal section of the needle-syringe assembly in FIG. 2 with the needle holder in the retracted position and the needle concealed by the barrel.

Reciprocating axial movement of the plunger 102 is limited by the available range of axial movement of the plunger 102 relative to the barrel 100 and the needle holder 108 (FIGS. 10–11). During normal use of the needle-syringe assembly, the lateral arm 144 of the needle holder 108 extends from the coaxial cavity 134 of the plunger 102, through the longitudinal slot 138 in the plunger 102, and through the distal portion of the oblique slot 114. The width of the longitudinal slot 138 is sized to accommodate the lateral arm 144. The length of the longitudinal slot 138 is preferably selected such that the length of the plunger cap 104 plus the length of the longitudinal slot 138 is substantially equal to the length between the apex 137 of the barrel 100 and the distal portion of the obique slot 114.

During normal use of the needle-syringe assembly, the barrel 100 and needle holder 108 are held stationary and the plunger 102 is free to move relative to the barrel 100 and the needle holder 108. The needle holder 108 is engaged to the barrel 100 by virtue of the taper lock between the distal cylindrical portion 133 and the nozzle 110 and the maintenance of the lateral arm 144 in the oblique slot 114 by the clamp 147. The plunger 102 is free to move relative to the needle holder 108 because the lateral arm 144 is not locked to the plunger 102 during normal use. The plunger 102 is free to move relative to the barrel 100 as long as the lateral arm 144 is free to move longitudinally through the longitudinal slot 138. The proximal and distal ends of the longitudinal slot 138 limit the available range of reciprocating relative axial movement of the plunger 102 (FIGS. 10–11). Due to the selected length of the longitudinal slot 138, forward axial movement of the plunger 102 is further limited by contact of the distal end 128 of the plunger cap 104 with the apex 137 of the barrel 100 (FIG. 10). With the foregoing arrangement of the lateral arm 144, the plunger 102 can move only in the axial direction, rotary movement being prevented by the positioning of the lateral arm 144 in both the longitudinal slot 138 in the plunger 102 and the oblique slot 114 in the barrel 100 and by the taper lock between the needle holder 108 and the barrel nozzle 110. The clamp engagement of the lateral arm 144 in the oblique slot 114 prevents displacement of the lateral arm 144 into the helical slot 140 and further inhibits rotary movement of the plunger 102.

In other words, during normal use the needle holder 108 is locked to the barrel 100 by the taper lock at the nozzle 110 and the fixed engagement of the lateral arm 144 within the oblique slot 114 by the clamp 147. At the same time, the plunger 102 is axially movable relative to the needle holder 108 because the coaxial cavity 134 and the longitudinal slot 138 permit the plunger 102 to slide over the leg and lateral arms 142, 144. As long as the lateral arm 144 of the needle holder 108 is located in the longitudinal slot 138 in the plunger 102, the needle-syringe assembly is in normal operative mode.

In the retraction mode of operation following normal use of the needle-syringe assembly, the needle 106 is retracted into the plunger 102 and the barrel 100 by axially moving the needle holder 108 toward the proximal end of the plunger 102. This is accomplished by first advancing the plunger 102, if it is not already fully advanced, into the barrel 100 so that the lateral arm 144 of the needle holder 108 moves to the proximal end of the longitudinal slot 138 (FIG. 10). The lateral arm 144 is disengaged from the oblique slot 114 of the barrel 100 by rotating the clamp 147 until the gap in the C-clamp is in annular alignment with the lateral arm 144 (FIG. 6b). Next, the plunger 102 and the lateral arm 144 of the needle holder 108 are rotated counterclockwise (as viewed from the proximal end) so that the plunger 102 applies a rotary force to the needle holder 108 and the oblique slot 114 simultaneously applies a proximally-directed longitudinal force to the needle holder 108. The compound rotary and longitudinal force releases the taper lock between the barrel nozzle 110 and the needle holder 108 and forces the lateral arm 144 to move proximally through the oblique slot 114. As the lateral arm 144 is forced proximally through the oblique slot 114, the needle holder 108 begins to retract into the coaxial cavity 134 in the plunger 102.

Continued rotary movement of the plunger 102 causes the lateral arm 144 to move from the oblique slot 114 to the travel slot 116 in the barrel 100 and from the longitudinal slot 138 to the helical slot 140 in the plunger 102. As the plunger 102 is still further rotated relative to the barrel 100, the lateral arm 144 moves through the remainder of the helical slot 140 in the plunger 102 without any further rotation of the needle holder 108. One rotation of the plunger 102 causes the lateral arm 144 to traverse the length of the single-revolution helical slot 140. During part of this continued rotation of the plunger 102, the lateral arm 144 moves proximally through the travel slot 116 until the lateral arm 144 reaches the proximal end of the barrel 100. The travel slot 116 prevents the lateral arm 144 from rotating relative to the barrel 100 so that the needle holder 108 does not rotate with the plunger 102.

Figure 2:
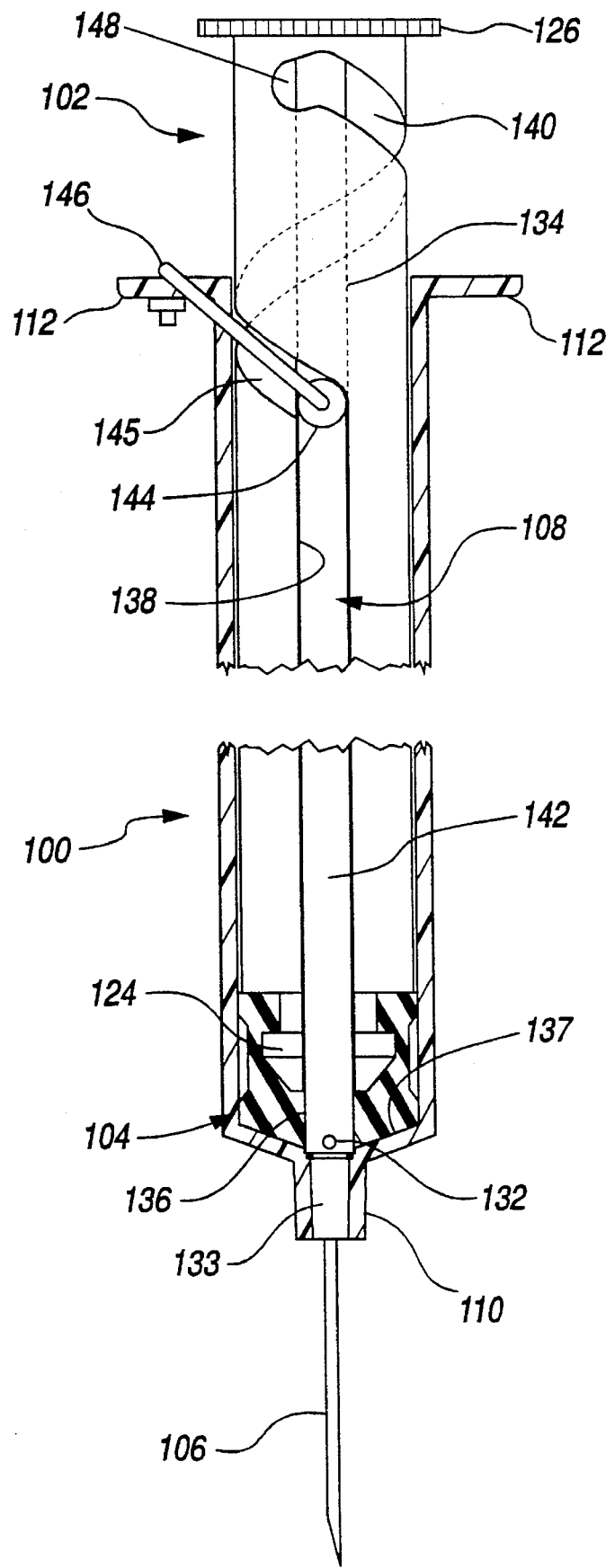
FIG. 2 is an enlarged longitudinal section of the needle-syringe assembly in FIG. 1 with the needle holder in a forward position.
Figure 4:
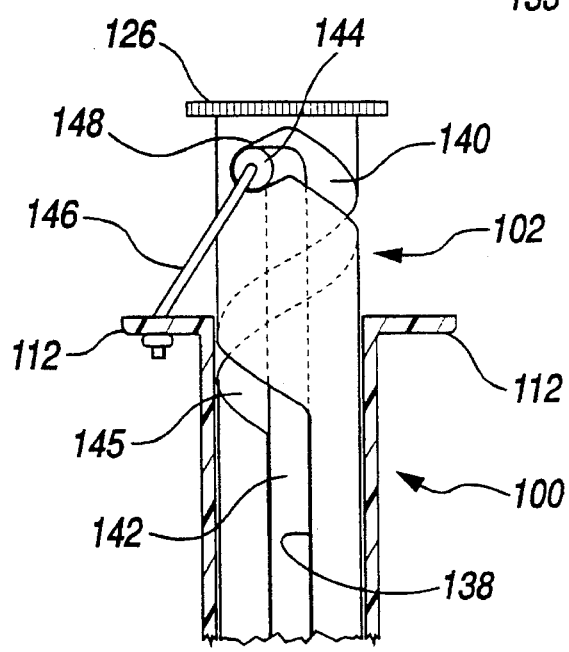
FIG. 4 is a fragmentary longitudinal section through a proximal portion of the needle-syringe assembly in FIG. 2 with the needle holder in a retracted position.
Figure 5:
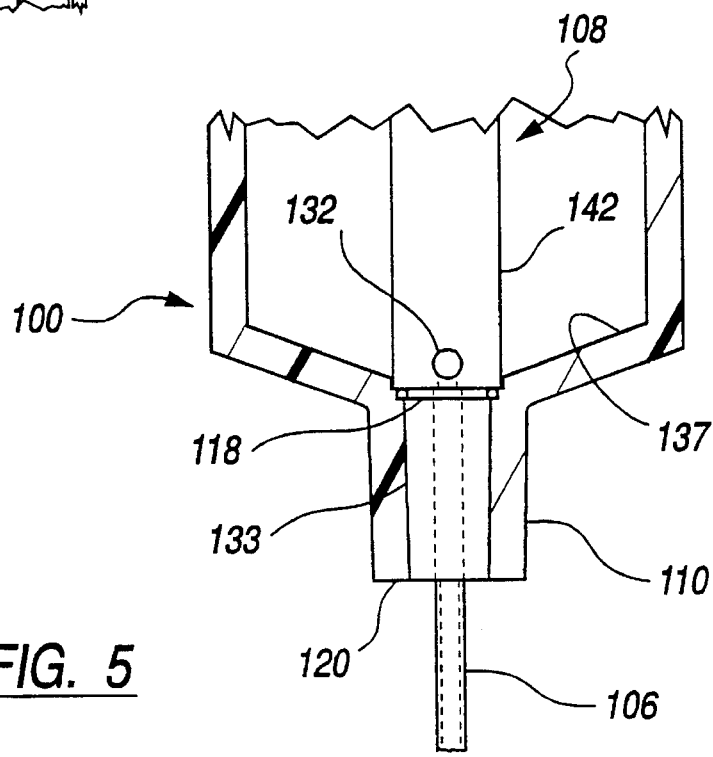
FIG. 5 is an enlarged fragmentary longitudinal section through a distal portion of the needle-syringe assembly in FIG. 2.

As the plunger 102 is further rotated, the lateral arm 144 exits the travel slot 116 and moves beyond the proximal end of the barrel 100. At this point, to limit rotation of the lateral arm 144 relative to the barrel 100, the assembly is provided with a flexible string 146 of elastomer or wire connecting the lateral arm 144 with the base plate 112 of the barrel 100 (FIGS. 2 and 4). Not only does the flexible string 146 limit rotation of the needle holder 108 relative to the barrel 100, but it also prevents the plunger 102 from being separated from the barrel 100 so that spillage of syringe contents does not occur.

When the lateral arm 144 of the needle holder 108 reaches the proximal end of the helical slot 140, retraction of the needle holder 108 and needle 106 is complete (FIG. 12). At the proximal end of the helical slot 140, a detente 148 traps the ascending lateral arm 144 of the needle holder 108. The needle holder 108 and most of the needle 106 are now locked inside the plunger cavity 134. The plunger 102 itself is locked to the barrel 100 by the flexible string 146 and the needle holder 108, and cannot undergo either rotary or reciprocal movements. As a result, the needle-syringe assembly is rendered inoperative and is ready for disposal. As illustrated in FIG. 12, in the retracted position the needle holder 108 is completely retracted inside the coaxial cavity 134 in the plunger 102, and the needle 106 is completely retracted and concealed inside the barrel 100. To assure that the needle 106 is completely inside the barrel 100, the longitudinal distance between the distal and proximal ends of the helical slot 140 is slightly greater than the exposed length of the hypodermic needle 106 when the plunger 102 is in its fully advanced position.

To operate the needle-syringe assembly, the protective cap is removed from the needle, and the required amount of medication is aspirated into the barrel 100. Next, the injection site on the body of a patient is determined and the skin is cleaned with an antiseptic solution. Following percutaneous entry of the needle into the patient, location of the needle tip in the vein is confirmed by aspirating a small amount of blood into the transparent barrel 100. The plunger 102 of the assembly is then advanced to force the medication from the barrel 100 into the vein. After the medication is administered, the needle 106 is withdrawn from the patient, the C-clamp 147 is released, and the base plate 126 of the plunger 102 is rotated counterclockwise until the lateral arm 144 of the needle holder 108 reaches the proximal end of the helical slot 140. The helical slot 140 may alternatively be configured to require clockwise, instead of counterclockwise, rotation of the plunger 102. With the needle 106 completely retracted inside the barrel 100, the needle-syringe assembly is discarded in its entirety.

In an alternative embodiment, the lateral arm 144 is L-shaped and is provided with a pin 151 connected orthogonal to the end of the longitudinal portion of the lateral arm 144 (FIG. 6a). Following needle retraction, the pin 151 prevents separation of the plunger 102 from the barrel 100 by engaging the base plate 112 of the barrel 100 at the proximal end of the longitudinal slot 116. The pin 151 prevents the end portion of the lateral arm 144 containing the pin 151 from moving proximally beyond the base plate 112 of the barrel 100.

Figure 8A:
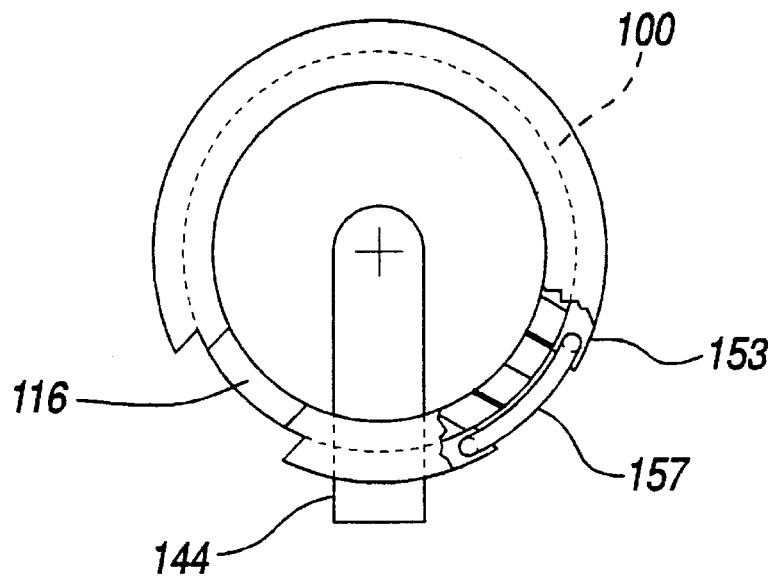
FIG. 8a is a cross-section of the needle-syringe assembly showing a collar for for disengaging the lateral arm of the needle holder from the oblique slot.
Figure 8B:
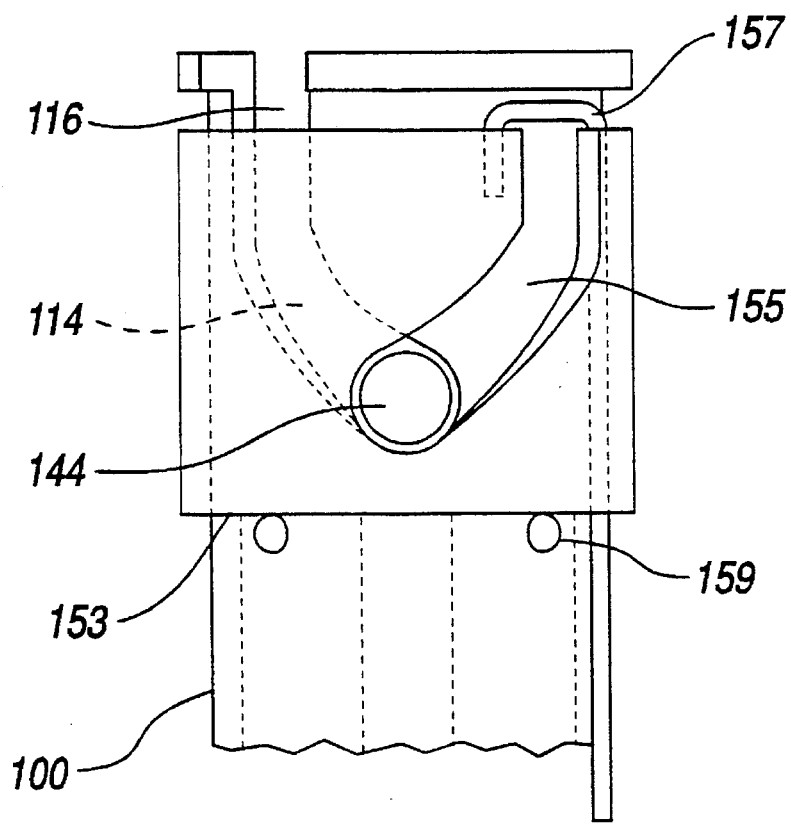
FIG. 8b is a fragmentary longitudinal section of the needle-syringe assembly showing the collar for disengaging the lateral arm of the needle holder from the oblique slot.

In another alternative embodiment, the distal cylindrical portion 133 of the needle holder 108 is disengaged from the nozzle 110 using a collar 153 rotatably mounted on the barrel 100 (FIGS. 8a and 8b). The collar 153 includes a slot 155 with an oblique portion and a longitudinal portion which counter the respective oblique slot 114 and longitudinal slot 116 in the barrel 100 as shown in FIG. 8b. The collar 153 is retained on the barrel 100 proximal to the pins 159 protruding outwardly from the barrel 100 adjacent the distal end of the collar 153. During normal use of the needle-syringe assembly, the lateral arm 144 of the needle holder 108 extends through the distal portion of the oblique slot 114 in the barrel 100 and the distal portion of the oblique portion of the collar slot 155. To initiate needle retraction, the collar 153 is rotated clockwise (as viewed from the proximal end). While rotating the collar 153 clockwise, the edge of the oblique portion of the collar slot 155 acts as a cam surface which disengages the distal cylindrical portion 133 of the needle holder 108 from the nozzle 110 and forces the lateral arm 144 to move proximally through the oblique slot 114. The lateral arm 144 is forced proximally through the oblique slot 114 by virtue of the "scissors-type" action between the oblique slot 114 and the collar slot 155.

When the lateral arm reaches the proximal end of the oblique slot 114, further needle retraction is accomplished in the manner previously described. That is, the plunger 102 is rotated to draw the lateral arm 144 through the longitudinal slot 116 in the barrel 100 while the lateral arm 144 moves proximally through the helical slot 140 in the plunger 102. As the lateral arm 144 exits the collar 153 via the longitudinal portion of the collar slot 155, the lateral arm engages a hook retaining member 157 slidably mounted in the collar 153. Continue rotation of the plunger 102 relative to the barrel 100 moves the lateral arm 144 proximally beyond the proximal end of the barrel 100. However, since the hook retaining member 157 is annularly fixed relative to the collar 153 and the collar 153 is now annularly fixed relative to the barrel 100, rotation of the lateral arm 144 is prevented due its engagement in the hook portion of the hook retaining member 157. The hook retaining member 157 is another means, besides the flexible string 146 and the longitudinal slot 116, for preventing rotation of the lateral arm 144 while rotating the plunger 102.

Figure 9A:
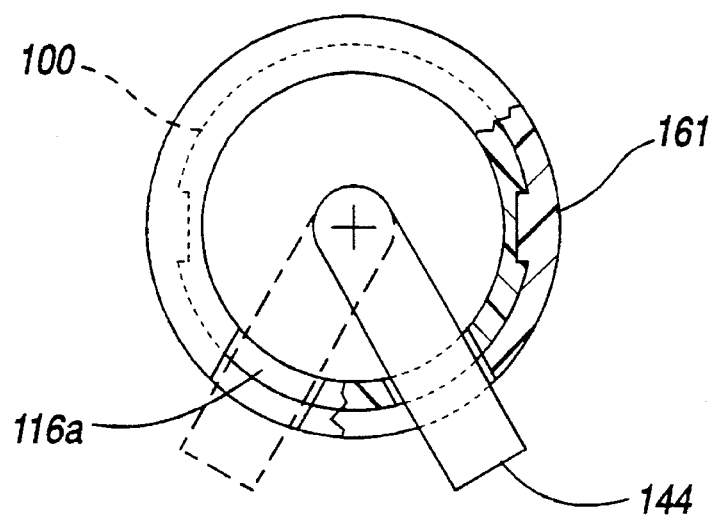
FIG. 9a is a cross-section of the needle-syringe assembly showing an alternative collar for disengaging the lateral arm of the needle holder from the oblique slot.
Figure 9B:
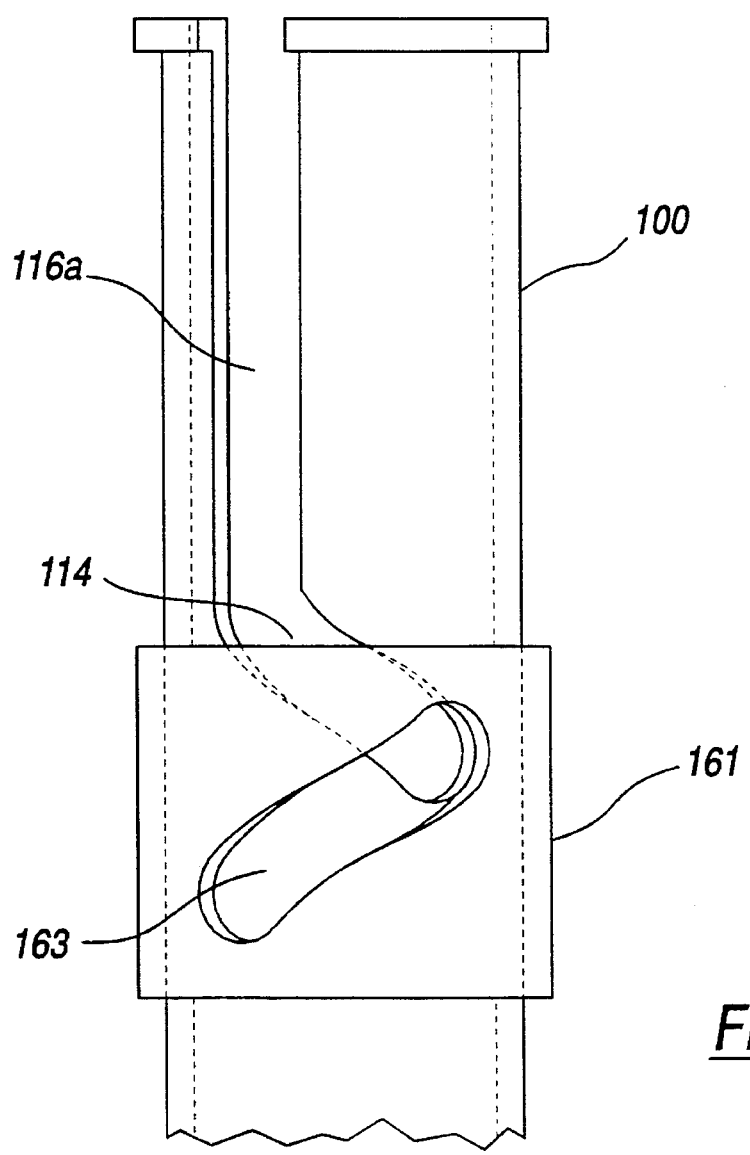
FIG. 9b is a fragmentary longitudinal section of the needle-syringe assembly showing the alternative collar for disengaging the lateral arm of the needle holder from the oblique slot.

In yet another alternative embodiment, a collar 161 is used in conjunction with an elongated longitudinal slot 116a in the barrel 100 to detach the engagement between the needle holder 108 and the barrel nozzle 110 and to prevent the lateral arm 144 from rotating with the plunger 102 during needle retraction (FIGS. 9a and 9b). The collar 161 is slidably mounted on the barrel 100 and includes an oblique slot 163 sloping in the opposite direction of the oblique slot 114 in the barrel 100. During normal use of the needle-syringe assembly, the lateral arm 144 protrudes through both the distal portion of the oblique slot 114 and the proximal portion of the oblique slot 163. To disengage the distal cylindrical portion 133 of the needle holder 108 from the barrel nozzle 110, the collar 161 is pulled toward the proximal end of the barrel 100. Such proximal movement of the collar 161 creates a "scissors-type" action which cams the lateral arm 144 proximally through the oblique slot 114 and distally through the oblique slot 163. After the lateral arm 144 reaches the proximal end of the oblique slot 114, the plunger 102 is rotated relative to the barrel 100 to continue needle retraction. While rotating the plunger 102, rotary movement of the lateral arm 144 relative to the barrel 100 is prevented by the elongated longitudinal slot 116a. The longitudinal slot 116a is of sufficient length to retain the lateral arm 144 as the lateral arm 144 moves through the entire helical slot 140 in the plunger 102.

As the manufacture of the needle-syringe assembly is fairly conventional, it will not be described herein in detail. It suffices to say that the needle holder 108 is preferably manufactured using injection molding of a high impact thermoplastic such as polypropeline or ABS, and the needle 106 is injection molded within the needle holder 108. The remaining components of the assembly, including the barrel 100, the plunger 102, and the cap 104, are manufactured using conventional techniques.

It can be seen from the foregoing description that the needle-syringe assembly performs all the conventional functions of injection syringes and yet, upon completion of injection, the hypodermic needle 106 is concealed within the barrel 100. The needle-syringe assembly can receive and inject medications any number of times into a particular patient by reciprocal longitudinal movement of the plunger 102 within the barrel 100. An unexpected advantage of the needle-syringe assembly is that its design prevents the plunger 102 from slipping out of the barrel 100 during normal use of the assembly. In some prior art designs, it is possible for the plunger to slip out of the barrel while withdrawing fluid from an injection vial, thereby spilling the medication out of the barrel. Not only does this waste medicine, but also the wasted medication might harm the administering physician or nurse.

Additionally, the needle-syringe assembly is easy to manufacture, cost-effective, and easy to use in the field. The cost-effectiveness of the assembly is reflected in the benefits provided by the assembly to the patient in general and the society in particular. The assembly is compact because the needle holder 108 is retracted directly into the plunger 102 itself. Because the needle holder 108 retracts into the plunger 102, the plunger 102 need not be fully extended for needle retraction to occur. Thus, when discarded following use, the needle-syringe assembly contributes minimally to the bulk of refuse. Since retraction of the needle 106 and the needle holder 108 are actuated at the base plate 126 of the plunger 102, the hand of a user does not come into the vicinity of the needle point, thereby minimizing the possibility of a needle prick during retraction. Moreover, the assembly employs substantially the same number of components as conventional syringes, and does not require additional guards, sheaths, sleeves, springs, etc. to conceal the needle 106 following use.

Referring next to FIGS. 13–17, the present invention further provides a guidewire insertion assembly. Since the construction of the guidewire insertion assembly is similar to the construction of the needle-syringe assembly, the guidewire insertion assembly will not be described herein in detail. It suffices to say that the guidewire insertion assembly has the same advantages as the needle-syringe assembly and is constructed from parts which are analogous to the parts of the needle-syringe assembly. These analogous parts are labelled in FIGS. 13–17 with reference numerals that vary from the reference numerals associated with the needle-syringe assembly by only the first digit. Thus, like the needle-syringe assembly, the guidewire insertion assembly includes a barrel 200 with a nozzle 210, a plunger 202 with a plunger cap 204, and a needle holder 208 with a hypodermic needle 206 connected thereto.

Figure 13:
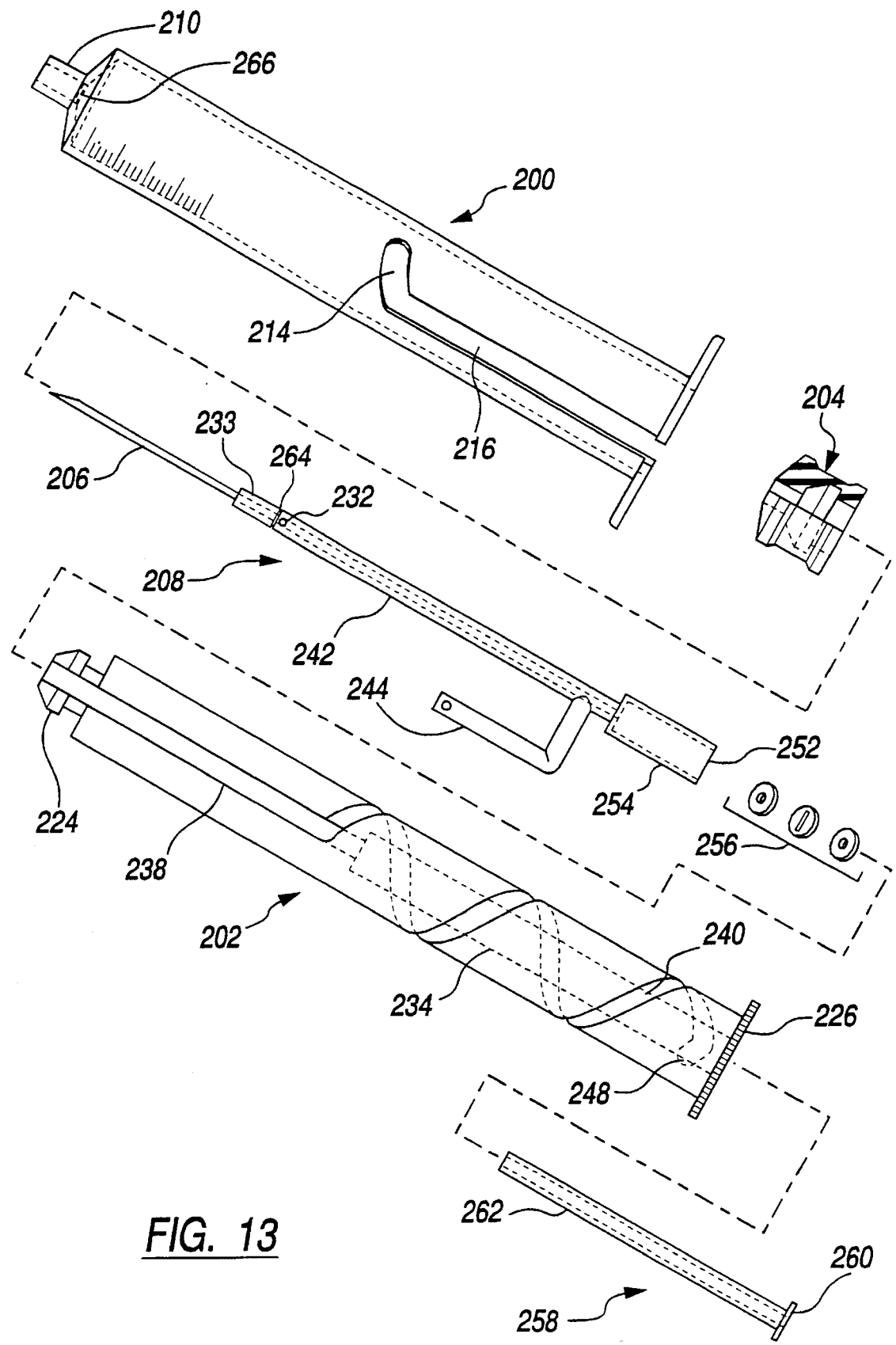
FIG. 13 is an exploded plan view of a guidewire insertion assembly embodying the present invention.

The differences between the guidewire insertion assembly and the needle-syringe assembly are discussed below. First, in order to accommodate a guidewire 250, the leg portion 242 of the needle holder 208 is hollow from one end to the other (FIG. 13). Also, the base plate 226 of the plunger 202 is provided with a central aperture which opens into the coaxial cavity 234 of the plunger 202. This allows the guidewire 250 to be inserted into the plunger cavity 234 via the central aperture in the base plate 226, and to be fed through the plunger cavity 234, through the hollow leg portion 242 of the needle holder 208, and through the needle 206 (FIG. 16). Second, the leg portion 242 of the needle holder 208 includes an expanded portion 254 having a conventional one-way slit valve 256 which permits the guidewire 250 to be passed through the valve 256 towards the hypodermic needle 206 (FIG. 13). At the same time, the valve 256 prevents any flash back of blood or entry of air through the valve 256 during insertion of the guidewire 250 into the vein of a patient. Moreover, the valve 256 prevents air from leaking into the vein. The proximal portion of the coaxial cavity 234 of the plunger 202 is widened to accommodate the expanded portion 254 of the needle holder 208.

Third, during normal use, the guidewire insertion assembly includes a tubular plastic sleeve 258 inserted into the coaxial cavity 234 in the plunger 202. The sleeve 258 has an outer diameter equal to the outer diameter of the expanded portion 254 of the needle holder 208, and the sleeve 258 has flanges 260 designed to fit flush with the base plate 226 of the plunger 202. The sleeve 258 contains a tapering channel 262 for accepting and feeding the guidewire 250 into the valve 256 within the expanded needle holder portion 254. The sleeve 258 straightens the guidewire 250 and permits it to pass through the valve 256, through the needle holder 208 and needle 206, and into the vein of a patient.

Figure 14:
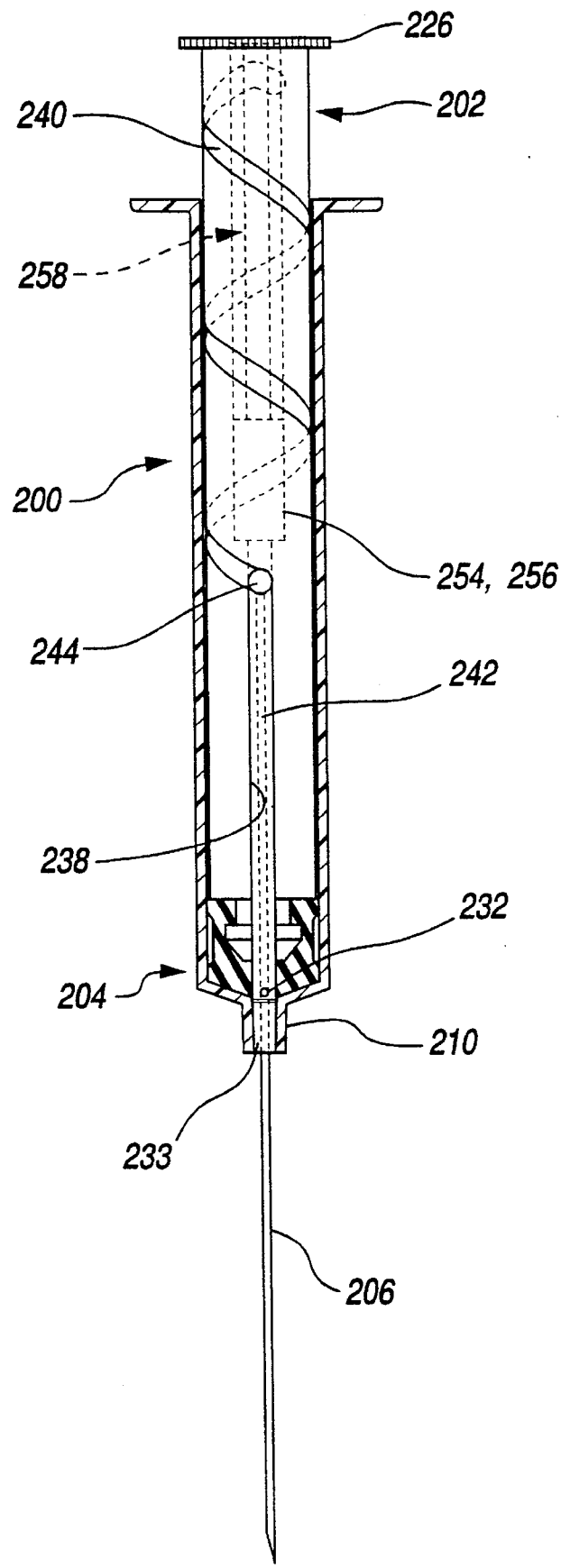
FIG. 14 is a longitudinal section of the guidewire insertion assembly in FIG. 13 with the needle holder in a forward position.
Figure 18:
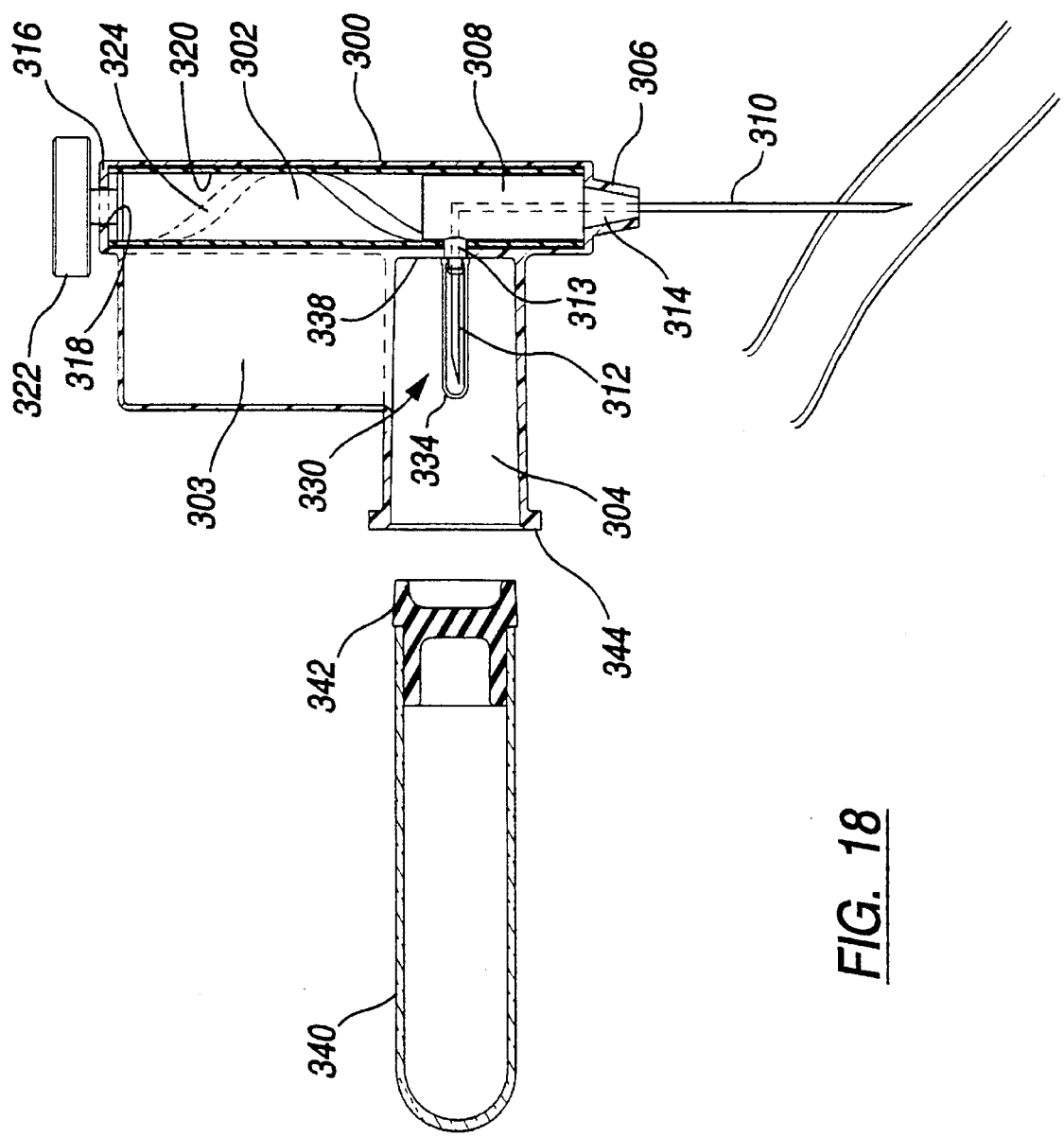
FIG. 18 is a longitudinal section of a blood sample collection assembly embodying the present invention.

Fourth, to improve performance, the dimensions of some of the parts of the guidewire insertion assembly are different from the dimensions of the analogous parts of the needle-syringe assembly (FIGS. 13–14). In particular, the needle holder 208 is shorter and the hypodermic needle 206 is shorter than the analogous needle holder 108 and needle 106 of the needle-syringe assembly. Furthermore, the longitudinal slot 238 is shorter and the helical slot 240 is longer than the longitudinal and helical slots 138, 140 of the needle-syringe assembly in order to retract the longer needle 206. Also, the barrel 200 and retainer slot 216 of the guidewire insertion assembly are longer than the associated barrel 100 and the travel slot 116 of the needle-syringe assembly.

To operate the guidewire insertion assembly, the protective cap of the hypodermic needle 206 is removed, the syringe is primed with normal saline, and the insertion site on the body of a patient is determined. Next, the skin at the insertion site is cleaned with an antiseptic solution and the needle tip is inserted into the vein of the patient (FIG. 15). The location of the needle tip in the vein is confirmed by aspirating a small amount of blood into the barrel 200. After returning the aspirated blood to the vein, the guidewire 250 is inserted in the plastic sleeve 258, passed through the valve 256 and the needle holder 208, and pushed until the guidewire 250 passes through the needle 206 and into the vein (FIG. 16). The insertion of the guidewire 250 into the vein using the guidewire insertion assembly is a relatively bleed free procedure. Following guidewire insertion, the needle 206 is withdrawn from the vein and the guidewire insertion assembly is slid backward over the guidewire 250.

Next, the C-clamp 247 is rotated relative to the barrel 200 to permit disengagement of the taper lock at the nozzle 210 and proximal movement of the lateral arm 244 through the oblique slot 214 in response to counterclockwise rotation of the plunger 226. The base plate 226 of the plunger 202 is further rotated counterclockwise until the lateral arm 244 of the needle holder 208 reaches the proximal end of the helical slot 240. As the needle holder 208 ascends the plunger cavity 234, the expanded portion 254 of the needle holder 208 pushes the sleeve 258 proximally so as to eject the sleeve 258 from the plunger cavity 234 (FIG. 17). The lateral arm 244 of the needle holder 208 is locked in the detente 248 at the proximal end of the helical slot 240. As in the needle-syringe assembly, the barrel 200 and the plunger 202 are interlocked by a flexible string to prevent their separation from one another. With the needle 206 retracted inside the barrel 200 and the plunger 202, the guidewire insertion assembly is discarded in its entirety.

Another embodiment of the present invention, illustrated in FIGS. 18–23b, provides a blood sample collection assembly including an integral external body 300 forming a first needle chamber 302, a second needle chamber 303, and a vacuum tube chamber 304. The axis of the first needle chamber 302 is orthogonal to the axis of the vacuum tube chamber 304. The first needle chamber 302 is a tubular or square hollow body having a hollow tapered conical nozzle 306 integrally connected to the distal end thereof. The nozzle 306 forms a locking female luer taper. The interior of the conical nozzle 306 communicates with the interior of the first needle chamber 302.

A cylindrical needle carrier 308, having either a double-ended hypodermic needle with a ninety degree bend or a pair of orthogonal hypodermic needles 310, 312 mounted therein, is disposed within the first needle chamber 302. The needle carrier 308 is displaceably interlocked to the first needle chamber 302 by a taper lock between the conically tapered portion 314 of the needle carrier 308 and the nozzle 306. The needle 310 protrudes from the distal end of the needle carrier 308 and is coaxial with the first needle chamber 302. Prior to using the blood sample collection assembly, the needle 310 is covered by a conventional protective cap (not shown) to prevent the sharp beveled point of the needle 310 from accidently puncturing someone. The needle 310 projects approximately one and one-quarter inches from the tapered portion 314 of the needle carrier 308.

The other needle 312 is integrally connected to and mounted ninety degrees away from the needle 310. During normal use, the needle 312 is positioned along the axis of the vacuum tube chamber 304 and the needle 312 protrudes from a side arm 313 of the needle carrier 308 into the vacuum tube chamber 304 at its base 338. In one embodiment, the needle 312 is a metallic hypodermic needle capable of penetrating a rubber stopper of a conventional vacuum tube. Alternatively, the needle 312 may be composed of plastic capable of penetrating a rubber stopper but incapable of penetrating skin, thereby eliminating the need for the second needle chamber 303. Such a plastic needle is manufactured and distributed by Baxter International of Deerfield, Ill. The use of the plastic needle reduces the possibility of accidental needle punctures by one-half. Since both of the needles 310, 312 are hollow, the interior of the needle 310 communicates with the interior of the needle 312 to form a continuous flow path between the needles.

Figure 20:
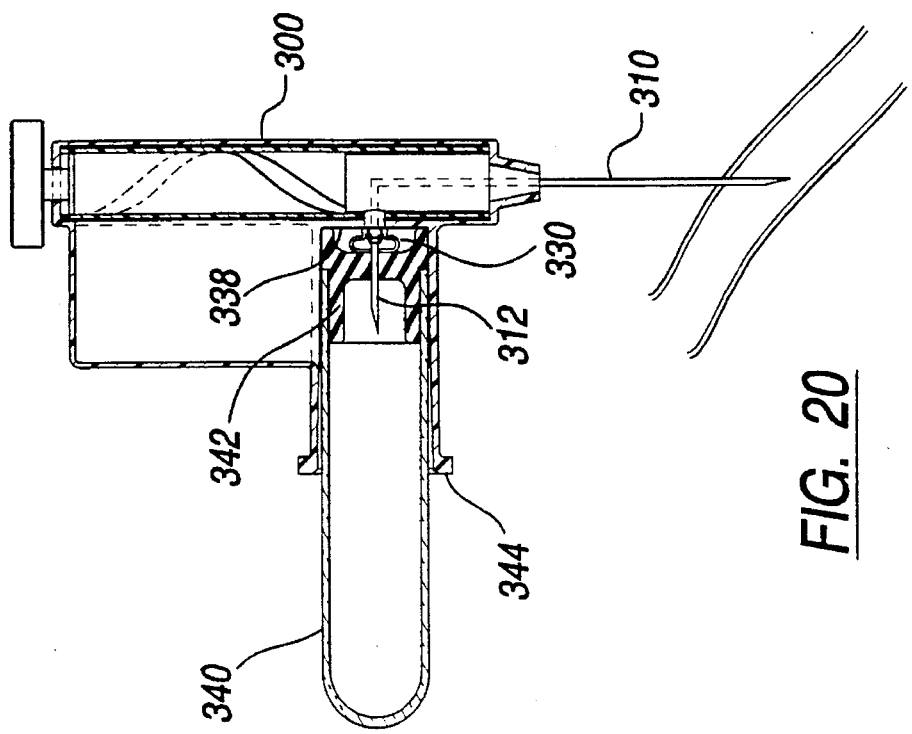
FIG. 20 is a longitudinal section of the blood sample collection assembly in FIG. 18 with the vacuum tube completely advanced within the vacuum tube chamber so that a needle of the assembly pierces the rubber stopper of the vacuum tube.
Figure 23A:
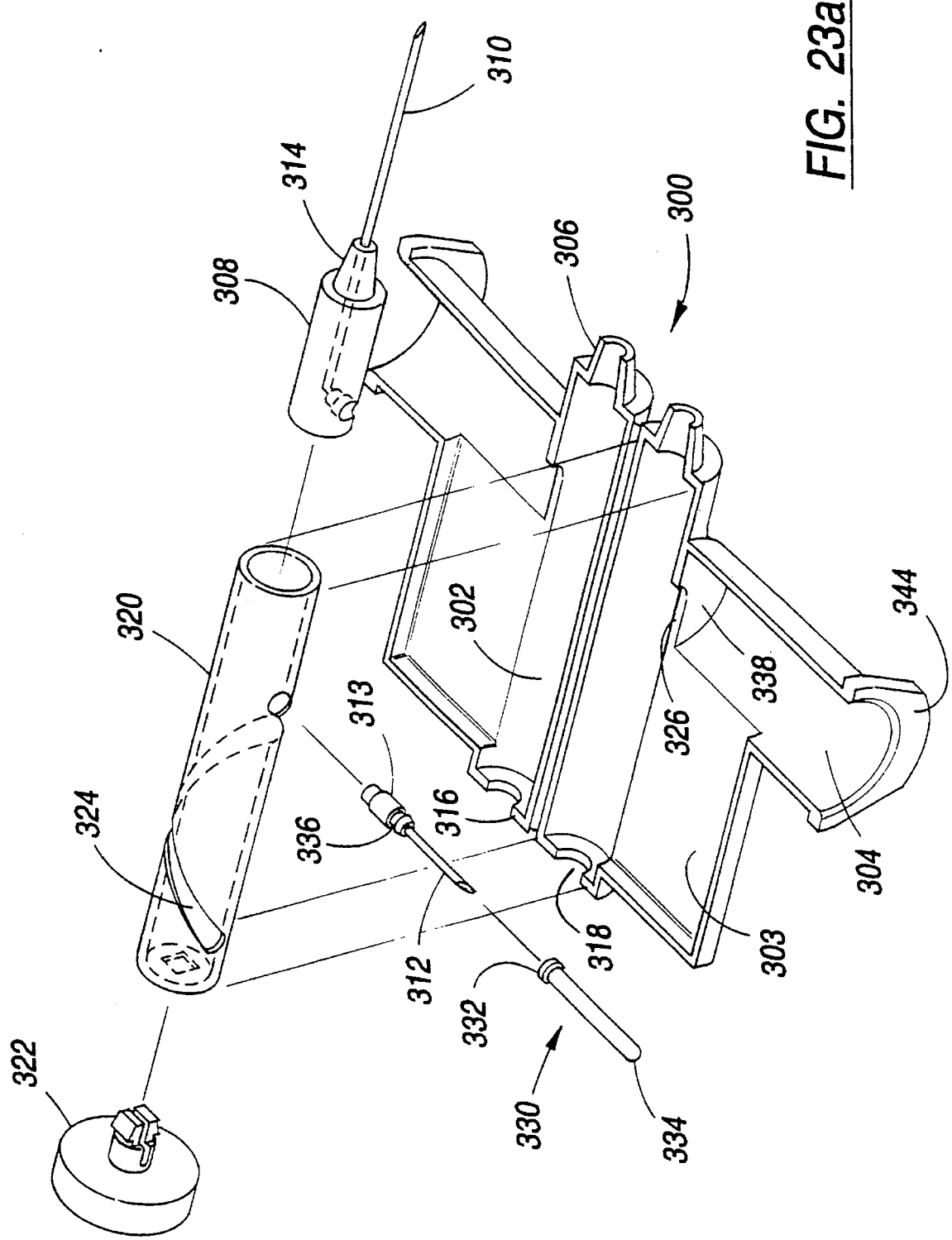
FIG. 23a is an exploded perspective view of the blood sample collection assembly in FIG. 18 showing that the external body is thermoformed from two polymeric constructions which are mirror images of one another.

The needle 312 is covered by a self-sealing rubber cap 330 having an open end 332 and a closed end 334 (FIG. 23a). The rubber cap 330 is retained in place by a plastic retaining ring 336 mounted on the circumference of the needle 312 (FIG. 23a). As a vacuum tube 340 is inserted into the vacuum tube chamber 304, the rubber stopper 342 of the vacuum tube 340 depresses the cap 330 so that the needle 312 pierces both the closed end 334 of the cap 330 and the rubber stopper 342 (FIG. 20). This allows blood entering the needles 310, 312 to pass into the vacuum tube 340. As the vacuum tube 340 is removed from the vacuum tube chamber 304, the cap 330 springs back to its position covering the needle 312 so as to check the flow of blood exiting from the needle 312. Thus, the rubber cap 330 acts as a valve which is opened by inserting a vacuum tube 340 into the vacuum tube chamber 304 and which is closed by removing the vacuum tube 340 from the vacuum tube chamber 304. The vacuum tube 340 recited herein may be any glass or plastic tube or tubular stem of a flask that is closed by a rubber stopper and contains a vacuum.

Figure 22:
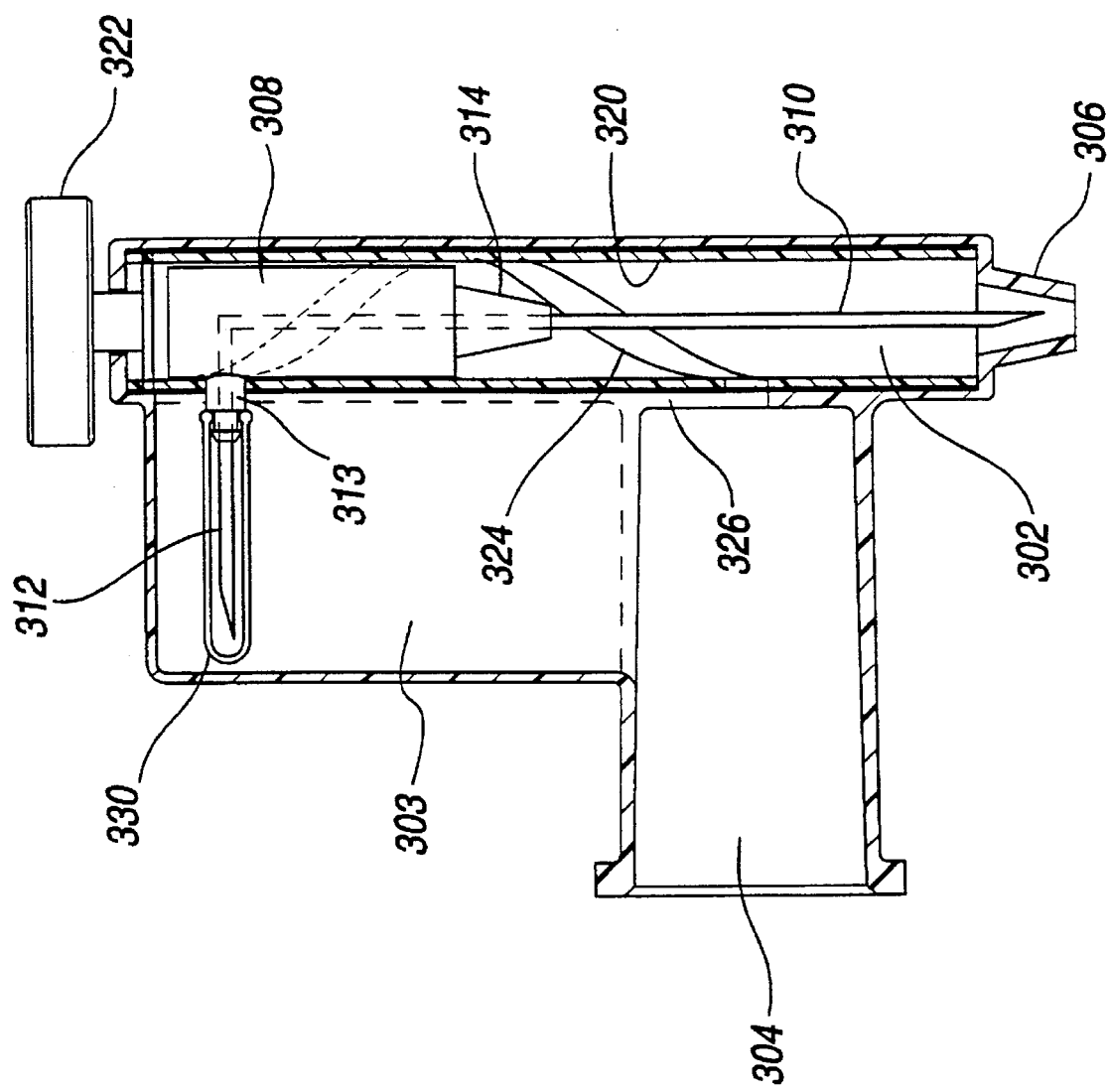
FIG. 22 is a longitudinal section of the blood sample collection assembly in FIG. 18 with the needle carrier and mounted needles in the retracted position.

Following normal use of the blood sample collection assembly, the needle carrier 308 is retracted toward the proximal end of the first needle chamber 302, thereby causing the needle 312 to retract into the second needle chamber 303 (FIG. 22). The second needle chamber 303 is preferably a generally rectangular body which is narrow is one transverse direction and relatively wide in the other transverse direction (see FIGS. 23a–23b). The transverse dimensions are sufficiently wide to accommodate the width and length of the needle 312. The longitudinal dimension of the second needle chamber 303 is sufficiently long to accommodate the needle 312 when the needle carrier 308 is fully retracted within the first needle chamber 302.

At the proximal end, the first needle chamber 302 forms a lid 316 having a circular lid aperture 318. Furthermore, an internal tube 320 is disposed within the first needle chamber 302, and the tube 320 is connected to a circular knob 322 via the lid aperture 318. Both the tube 320 and the circular knob 322 are coaxial with the first needle chamber 302, and rotation of the circular knob 322 relative to the first needle chamber 302 causes the tube 320 to rotate relative to the first needle chamber 302. The circular knob 322 preferably includes a textured longitudinal surface to permit the knob 322 to be easily gripped and rotated. The length of the internal tube 320 matches the internal longitudinal dimension of the first needle chamber 302 to prevent axial movement of the tube 320 relative to the first needle chamber 302. Moreover, the outer diameter of the internal tube 320 is slightly smaller than the inner diameter of the first needle chamber 302 to permit the internal tube 320 to rotate freely, yet stably, relative to the first needle chamber 302.

Rotation of the internal tube 320 relative to the first needle chamber 302 causes the needle carrier 308 to move axially within the first needle chamber 302 from a forward position to a retracted position. In FIG. 21c, the forward position of the needle carrier 308 is depicted in solid lines, while the retracted position is depicted in dotted lines. Axial movement of the needle carrier 308 relative to the first needle chamber 302 is effected using a helical slot 324 in the circumferential wall of the internal tube 320 in conjunction with a longitudinal slot 326 in the wall of the first needle chamber 302. The helical slot 324 and longitudinal slot 326 are positioned such that the side arm 313 of the needle carrier 308 extends through both the distal end of the helical slot 324 and the distal end of the longitudinal slot 326 when the needle carrier 308 is in the forward position (FIG. 21a). Similarly, when the needle carrier 308 is in the retracted position, the side arm 313 extends through both the proximal end of the helical slot 324 and the proximal end of the longitudinal slot 326. From the foregoing arrangement, it can be seen that the distal end of the longitudinal slot 326 overlies the distal end of the helical slot 324 when the needle carrier 308 is in the forward position, and the proximal end of the longitudinal slot 326 overlies the proximal end of the helical slot 324 when the needle carrier 308 is in the retracted position.

During retraction of the needle carrier 308, the first needle chamber 302 is held stationary while the internal tube 320 is rotated using the circular knob 322. While the internal tube 320 is being rotated, the needle carrier 308 is prevented from rotating with the internal tube 320 by virtue of the extension of the side arm 313 through the longitudinal slot 326 in the first needle chamber 302. Instead of rotating, the needle carrier 308 moves axially through the first needle chamber 302. More specifically, axial movement of the needle carrier 308 is controlled by the movement of the side arm 313 through the helical slot 324 in the rotating tube 320. As the side arm 313 moves through the helical slot 324, the side arm 313 cannot rotate or "swing" with the internal tube 320 because the side arm 313 is lodged in the longitudinal slot 326. Instead, the side arm 313 is forced to ascend the longitudinal slot 326 until the side arm 313 reaches the proximal end of the helical slot 324 (FIG. 22). At the proximal end of the helical slot 324, there is a detente 328 for engaging the ascending side arm 313, thereby locking the needle carrier 308 in the retracted position.

Figure 19:
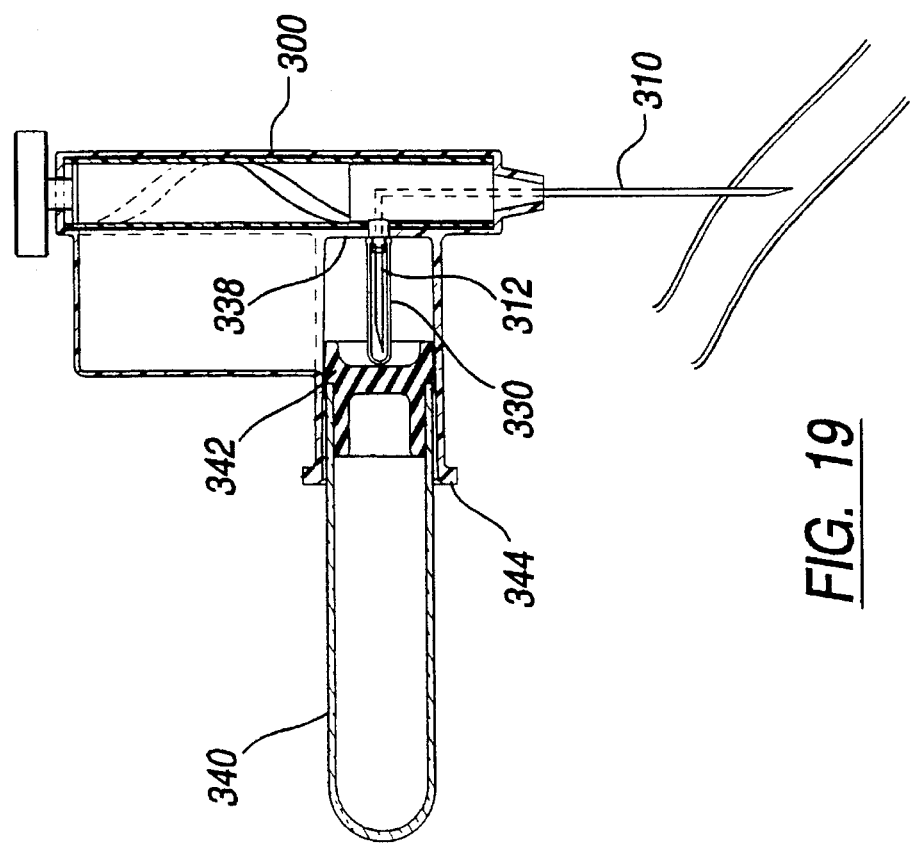
FIG. 19 is a longitudinal section of the blood sample collection assembly in FIG. 18 with the vacuum tube partially advanced within the vacuum tube chamber.

To operate the blood sample collection assembly, the protective cap is removed, the blood sample collection site on the body of a patient is determined, and the skin is cleaned with an antiseptic solution. The needle 310 is then entered into the vein of the patient. To collect a blood sample, the vacuum tube 340 with the rubber stopper 342 is inserted into the vacuum tube chamber 304 (FIGS. 19–20). After the vacuum tube 340 is filled with the desired amount of blood, the vacuum tube 340 is removed from the vacuum tube chamber 304. Additional blood may be collected by inserting, filling, and removing additional vacuum tubes. The vacuum tube chamber 304 includes tabs 344 for providing leverage while pushing a vacuum tube over the point of the needle 312 to puncture the rubber stopper of the vacuum tube. While inserting a vacuum tube, the orthogonal orientation of the vacuum tube chamber 304 relative to the first needle chamber 302 compels that the vacuum tube be pushed into the vacuum tube chamber 304 in a direction toward a stabilizing hand, rather in the direction of the sharp point of the needle 310 located in the vein. Next, the needle 310 is withdrawn from the vein. The circular knob 322 is rotated until the needle carrier 308 is completely retracted with the side arm 313 locked in the detente 328 (FIG. 22). With the needle carrier 308 in the retracted position, the needle 310 is concealed by the first needle chamber 302 and the needle 312 is concealed by the second needle chamber 303. Finally, the blood sample collection assembly is discarded in its entirety.

It can be seen from the foregoing description that the blood sample collection assembly avoids the situation of advancement of one sharp point of a double-pointed needle towards an operator while retraction of another point of the double-pointed needle is attempted. In particular, since the needle 312 is orthogonal to the needle 310, the side of the needle 312, instead of the point of the needle 312, is advanced toward an operator while the needle 310 is retracted into the first needle chamber 302. Moreover, both needles 310, 312 are retracted and concealed by operating a single mechanism, the circular knob 322. Due to the orthogonal orientation of the vacuum tube chamber 304 relative to the first needle chamber 302, insertion of a vacuum tube is accomplished by pushing the vacuum tube in the direction of a stabilizing hand of an operator, rather than in the direction of the needle in the vein. This reduces the possibility of imparting forward thrust on the needle in the vein which, in turn, minimizes the possibility of double puncturing the vein. Furthermore, the blood sample collection assembly is compact because the needle carrier 308 is retracted directly into the internal tube 320 itself. Because the needle carrier 308 retracts into the internal tube 320, the internal tube 320 need not extended beyond the proximal end of the first needle chamber 302 for needle retraction to occur. Thus, when discarded following use, blood sample collection assembly contributes minimally to the bulk of refuse. The blood sample collection assembly is also compact because, with the needles 310, 312 mounted orthogonal to one another, the length of the assembly is shorter than existing blood sample collection assemblies.

Figure 23B:
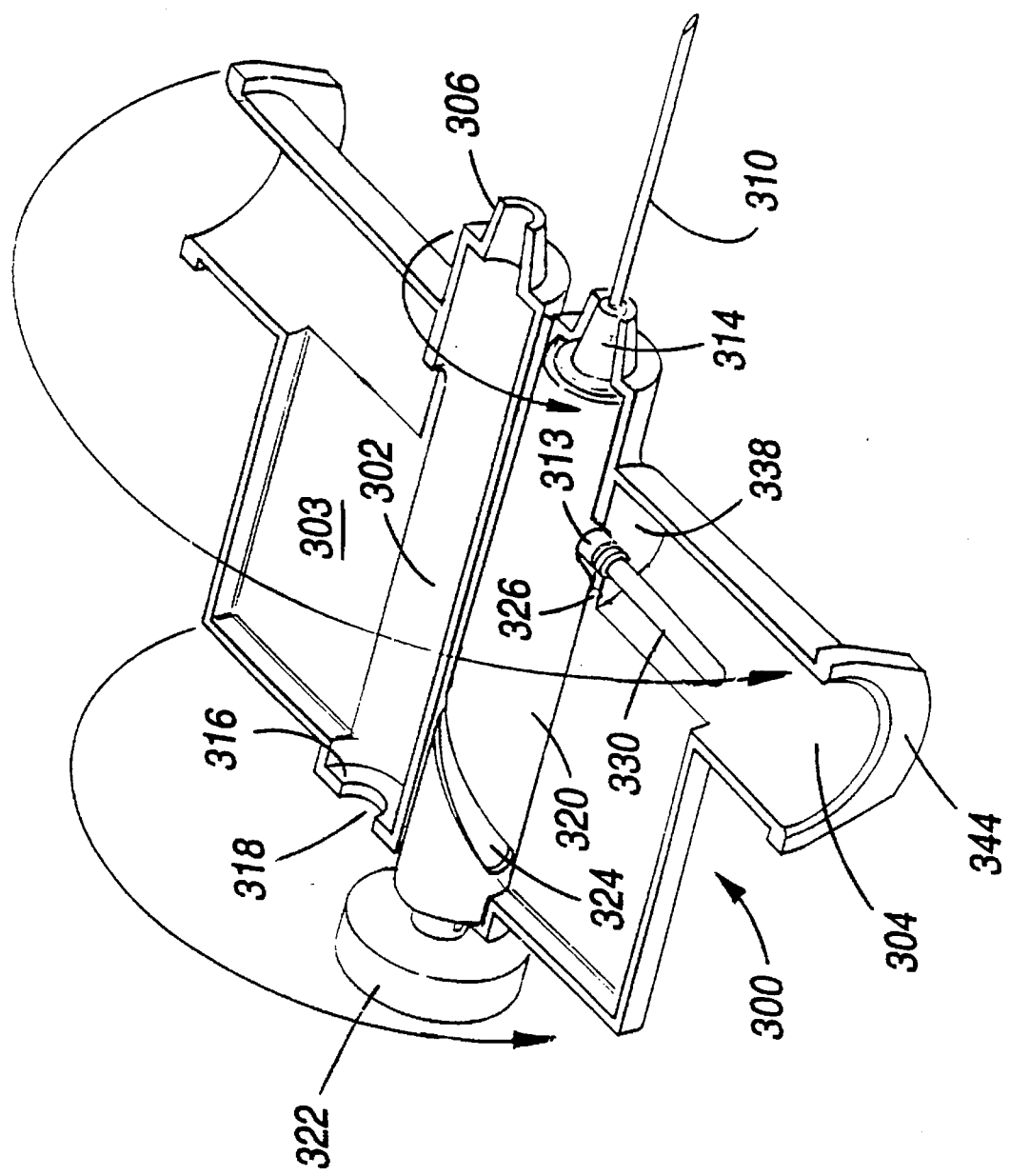

Referring to FIGS. 23a–23b, the blood sample collection assembly is constructed by injection molding the entire assembly from organic polymers, preferably thermoplastics such as a polypropeline or ABS. To construct the needle chambers 302, 303 and the vacuum tube chamber 304, a polymeric sheet is thermoformed to represent a single piece, mirror image, isometric half of these elements. Next, the internal tube 320 with the mounted knob 322 and the needle carrier 308 with the mounted needles 310, 312 are positioned at the proper location on the thermoformed sheet, and the thermoformed sheet is folded and secured shut by interlocking detents on the contacting surfaces (FIG. 23b). For additional safety an ultrasonic or solvent bond is created at the areas of contact to maintain the integrity of the assembly. The assembly is sterilized by conventional means.

Figure 26:
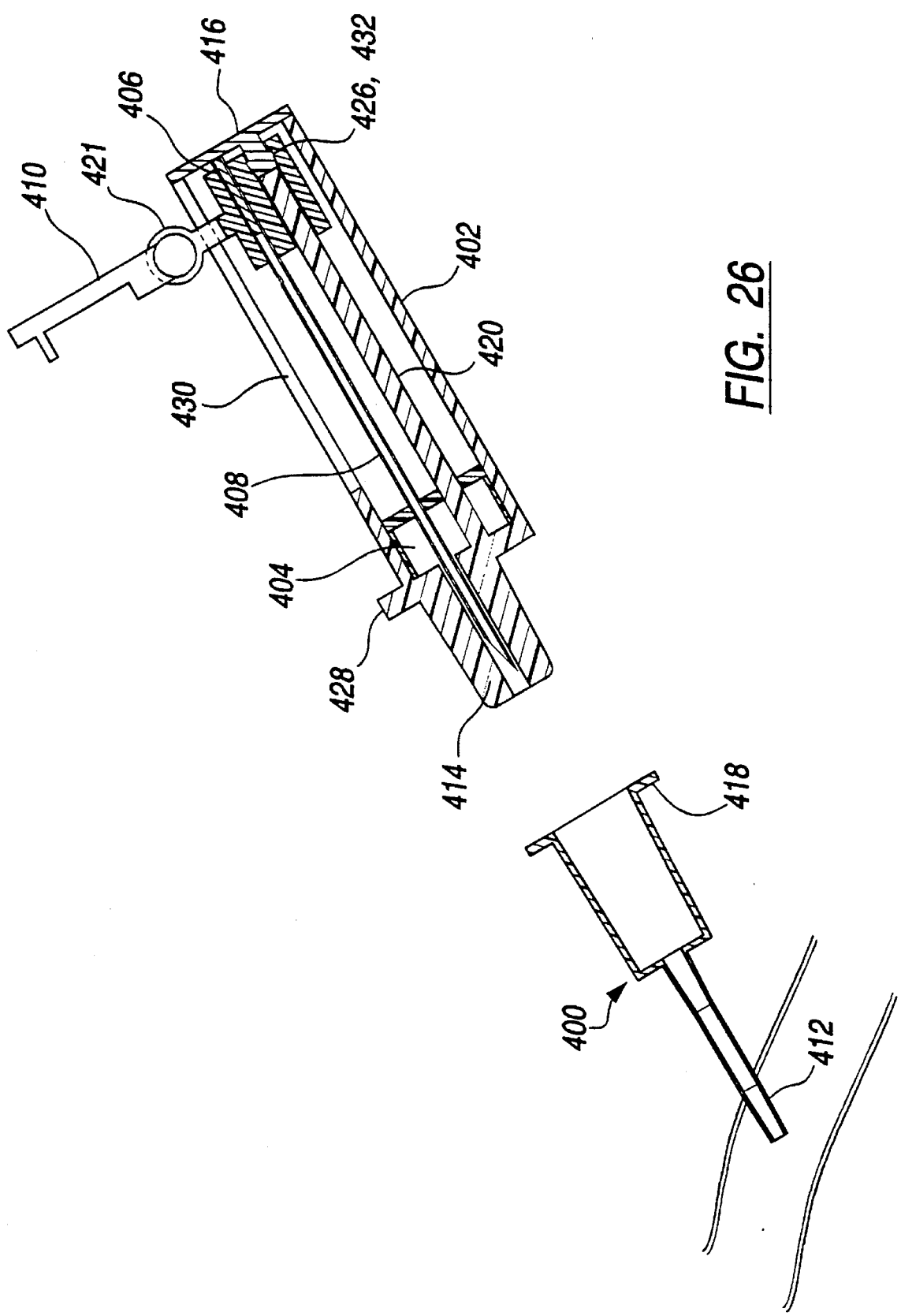
FIG. 26 is a cross-section of the over-the-needle catheter assembly in FIG. 24 with the needle carrier and mounted needle in the retracted position.

FIGS. 24–26 depict an OTN catheter assembly including an OTN catheter 400, a needle chamber 402, a flashback chamber 404, a needle carrier 406 with a hypodermic needle 408 mounted therein, and a latch 410 connected to the needle carrier 406. In the preferred embodiment, the OTN catheter 400 is a polymeric catheter having a feathered tip 412 mounted thereto. The needle chamber 402 is a tubular or square body with a distal conical nozzle 414 and proximal cover plate 416. The distal outer surface of the needle chamber 402 has prominent textured markings to permit a user to frictionally grip the chamber during insertion of the needle 408 and catheter 400 into a vein. During normal use of the OTN catheter assembly, the hub 418 of the OTN catheter 400 is coaxially mounted over the nozzle 414 and the hypodermic needle 408 protrudes through both the nozzle 414 and the OTN catheter 400. The feathered tip 412 of the catheter 400 promotes an easy advance of the catheter 400 over the needle 408. Prior to inserting the needle 408 and catheter tip 412 into a vein, the needle 408 and catheter tip 412 are enclosed by a removable cap (not shown).

The needle chamber 402 contains an integral linear track 420 to enable precise axial movement of the needle carrier 406 along the track 420. The needle carrier 406 contains an axial cavity 422 with dimensions that approximately match the dimensions of the linear track 420 in the needle carrier 406 with reasonable play to allow for precise axial movement of the needle carrier 406 along the track 420. In particular, both the cavity 422 and the linear track preferably have trapezoidal, oval, or other non-rotatable cross-sections, and the dimensions of the cavity 422 are slightly greater than the associated dimensions of the linear track 420 (FIG. 25). Thus, the linear track 420 stabilizes the needle carrier 406 in relation to the needle chamber 402. Alternatively, the needle carrier 406 may be designed to ride and slide on the inner surface of the needle chamber 402. Forward movement of the needle carrier 406 is limited by its contact with a partition disc 424 which forms the rear wall of the flashback chamber 404. If a flashback chamber 404 is not included in the assembly, forward movement of the needle carrier 406 is limited by its contact with the face plate 428 of the nozzle 414. Rearward movement of the needle carrier 406 is limited by detentes 426, located on the linear track 420, over which the needle carrier 406 is irretrievably locked when retracted.

The latch 410 is a ring latch pivotally mounted on a flange 421 of the needle carrier 406, and the latch 410 permits the needle carrier 406 to be locked in either a forward position or a retracted position. Prior to and during normal use of the OTN catheter assembly, the latch 410 retains the hub 418 of the OTN catheter 400 against the face plate 428 of the needle chamber 402 so as to lock the needle carrier 406 in the forward position (FIG. 24). Following puncture of the vein of a patient and insertion of the OTN catheter 400 into the vein, the latch 410 is disengaged from the hub 418 of the OTN catheter 400. The latch 410 is retracted through a longitudinal slot 430 in the needle chamber 402, thereby causing the needle carrier 406 and the mounted needle 408 to be retracted. Retraction of the needle carrier 406 and needle 408 is complete when detentes 432 on the needle carrier 406 engage the detentes 426 on the linear track 420. At this retracted position the needle carrier 406 is irretrievably locked to the linear track 420 with the needle 408 positioned inside the needle chamber 402 (FIG. 26). The OTN catheter 400 is then dislodged from the nozzle 414 and advanced into the vein.

The purpose of the hinge-type latch 410 is to mechanically unify the needle chamber 402 with the needle carrier 406 so that insertion force applied to the needle chamber 402 is directly transmitted to the hypodermic needle 408 and catheter 400. Release of the latch 410 disassociates this mechanical unity, permitting the needle carrier 406 to be retracted within the needle chamber 402 and locked in the retracted position. In an alternative embodiment, similar force transmission and disassociation is achieved using a lever-type latch 438 which engages in a T-shaped slot having proximal and distal transverse portions 440, 442 and a longitudinal portion 444 connected therebetween (FIG. 27–29). The needle carrier 406 is locked in the forward position by engaging the latch 438 in the distal transverse portion 442 of the slot. Disengagement of the latch 438 from the distal transverse portion 442 of the slot permits the latch 438 to slide axially rearward through the longitudinal portion 444 of the slot. Since the needle carrier 406 is attached to the latch 438, rearward axial movement of the latch 438 causes corresponding rearward axial movement of the needle carrier 406. The needle carrier 406 is locked in the retracted position by engaging the latch 438 in the proximal transverse portion 440 of the slot.

During puncture of the vein, confirmation that the needle 408 and catheter tip 412 are located in the vein can be made by viewing blood entering the catheter 400 by capillary action. It, however, is preferable to provide the OTN catheter assembly with the flashback chamber 404 to assure that continuity between the needle 408 and the vein is established. The flashback chamber 404 is incorporated in the OTN catheter assembly by inserting the partition disc 424 just distal to the forward position of the needle carrier 406. The partition disc 424 is retained in the needle chamber 402 by a limit stop 446 extending between the partition disc 424 and the face plate 428. The partition disc 424 has outer dimensions matching the inner dimensions of the needle chamber 402, and the disc 424 has longitudinal openings sized to allow snug passage therethrough of the linear track 420 and the hypodermic needle 408. The hypodermic needle 408 contains a side aperture 434 which opens up into the flashback chamber 404. Confirmation of proper insertion in the vein is indicated by blood entering the flashback chamber 404 via the side aperture 434 in the needle 408. The axial cavity 420 for the linear track 422 vents the flashback chamber 404 to permit this entry of blood into the chamber 404.

The OTN catheter assembly is preferably made by a conventional thermoplastic injection molding process. To begin with, the needle chamber 402, including the nozzle 414, body, and linear track 420, are molded as a single unit. The partition disc 424 is separately molded from thermoplastic polymer with dimensions which allow the disc 424 to tightly fit within the needle chamber 402. The disc 424 is inserted into the needle chamber 402 to generate the flashback chamber 404. The longitudinal slot 430 is generated by providing an elevation in the mold cavity. Furthermore, while the needle carrier 406 is molded by an injection molding process, the hypodermic needle 408 is insert molded within the needle carrier 406. Alternatively, the hypodermic needle 408 with the side aperture 434 is bonded within the needle carrier 406 after the needle carrier 406 is molded. Next, the needle carrier 406 is inserted into the needle chamber 402, and the molded latch 410 is engaged with the flange 421 of the needle carrier 406. The needle chamber 402 is closed by engaging detentes 436 on the separately molded or integrally molded and folded proximal plate 416 with mating detentes on the needle chamber 402 and the linear track 420.

To use the OTN catheter assembly, the skin of a patient is first prepared and a peripheral vein is made prominent. Under aseptic precautions the vein is punctured with the needle 408 and catheter 400 of the assembly, and the location of the needle tip is judged by the change in color under the catheter or by the appearance of blood in the flashback chamber 404. Once the location of the needle tip is confirmed, the latch 410 is disengaged and slid rearward through the longitudinal slot 430. This action retracts the needle carrier 406 until the detentes 432 on the needle carrier 406 are engaged with the detentes 426 on the linear track 420. While advancing and retaining the OTN catheter 400 in the vein, the remainder of the assembly is removed and an intravenous line is connected to the catheter 400. Finally, the catheter hub 418 is secured to the skin of the patient by adhesive tape.

While the present invention has been described with reference to one or more particular embodiments, those skilled in the art will recognize that many changes may be made thereto without departing from the spirit and scope of the present invention. For example, the rotary-type retraction mechanism for the blood sample collection assembly may be replaced with a linear-type mechanism similar to that employed in connection with the OTN catheter assembly. In particular, instead of using the internal tube 320 with the helical slot 324 and the circular knob 322, the needle carrier 308 is provided with an axial cavity that slidably engages a linear track contained in the first needle chamber 302. A latch connected to the needle carrier 308 via a longitudinal slot in the first needle chamber 302 is used to engage the needle carrier 308 in the forward (non-retracted) position. To retract the needle carrier 308, the latch is disengaged and moved longitudinally through the longitudinal slot. Retraction of the needle carrier 308 is complete when detentes on the needle carrier 308 engage mating detentes on the linear track.

Another modification is to replace the linear-type retraction mechanism for the OTN catheter assembly with the rotary-type mechanism employed in connection with the preferred embodiment of the blood sample collection assembly. Instead of using the latch 410, the linear track 420, and the axial cavity 422, the needle chamber 402 is provided with an internal tube containing a helical slot. A side arm on the needle chamber 402 extends through both the helical slot and the longitudinal slot 430 in the needle chamber 402. Rotation of the internal tube is effected by a circular knob connected to the proximal end of the internal tube. Such rotation of the internal tube causes the needle carrier 406 to be retracted within the needle chamber 402. Each of these embodiments and obvious variations thereof is contemplated as falling within the spirit and scope of the claimed invention, which is set forth in the following claims.

What is claimed is:

1. An over-the-needle catheter assembly operable in a normal mode and convertible to a retraction mode, comprising:

an elongated, generally cylindrical needle chamber forming a hollow nozzle located at the distal end of the needle chamber and opening into the interior of the needle chamber, said needle chamber having a longitudinal slot formed in the cylindrical wall of said needle chamber;

a needle carrier slidably mounted within said needle chamber for movement between a forward position and a retracted position, said needle carrier having a hollow needle mounted thereon, said needle protruding through said nozzle when said needle carrier is in said forward position, said needle being concealed by said needle chamber when said needle carrier is in said retracted position; and latch means coupled to said needle carrier through said longitudinal slot, said latch means being engaged to said needle chamber to lock said needle carrier in said forward position during the normal mode and being disengaged from said needle chamber during the retraction mode, said latch means securing an over-the-needle catheter to said needle chamber during the normal mode said latch means including a hinge pivotally mounted on said needle carrier, and securing the hub of the over-the-needle catheter to said needle chamber to lock said needle carrier in said forward position during the normal mode.

2. The catheter assembly of claim 1, wherein said hinge disengages the hub of the over-the-needle catheter from said needle chamber during the retraction mode.

3. The catheter assembly of claim 1, wherein said hinge secures the hub of the over-the-needle catheter to the outer surface of said nozzle to lock said needle carrier in said forward position during the normal mode.

4. An over-the-needle catheter assembly operable in a normal mode and convertible to a retraction mode, comprising:

an elongated, generally cylindrical needle chamber forming a hollow nozzle located at the distal end of the needle chamber and opening into the interior of the needle chamber, said needle chamber having a longitudinal slot formed in the cylindrical wall of said needle chamber;

a needle carrier slidably mounted within said needle chamber for movement between a forward position and a retracted position, said needle carrier having a hollow needle mounted thereon, said needle protruding through said nozzle when said needle carrier is in said forward position, said needle being concealed by said needle chamber when said needle carrier is in said retracted position;

an over-the-needle catheter mounted over said nozzle during the normal mode and disengaged from said nozzle during the retraction mode;

a hinge pivotally mounted on said needle carrier through said longitudinal slot, said hinge being engaged to said needle chamber to lock said needle carrier in said forward position during the normal mode and being disengaged from said needle chamber during the retraction mode; and locking means for locking said needle carrier in said retracted position.

5. The catheter assembly of claim 4, wherein said hinge includes means for securing said over-the-needle catheter to said nozzle during the normal mode.

6. The catheter assembly of claim 5, wherein said securing means secures the hub of the over-the-needle catheter to said nozzle during the normal mode.

7. The catheter assembly of claim 6, wherein said securing means disengages the hub of the over-the-needle catheter from said nozzle during the retraction mode.

8. The catheter assembly of claim 4, wherein said needle chamber includes a linear track in the interior thereof and said needle carrier is slidably mounted on said linear track.

9. The catheter assembly of claim 8, wherein said locking means includes a detente located on said needle carrier which engages with a mating detente located at the proximal end of said linear track.

10. An over-the-needle catheter assembly operable in a normal mode and convertible to a retraction mode, comprising:

an elongated, generally cylindrical needle chamber forming a hollow nozzle located at the distal end of the needle chamber and opening into the interior of the needle chamber, said needle chamber having a longitudinal slot formed in the cylindrical wall of said needle chamber;

a needle carrier slidably mounted within said needle chamber for movement between a forward position and a retracted position, said needle carrier having a hollow needle mounted thereon, said needle protruding through said nozzle when said needle carrier is in said forward position, said needle being concealed by said needle chamber when said needle carrier is in said retracted position;

a hinge pivotally mounted on said needle carrier through said longitudinal slot, said hinge being engaged to said needle chamber to lock said needle carrier in said forward position during the normal mode and being disengaged from said needle chamber during the retraction mode;

locking means for locking said needle carrier in said retracted position; and a transverse partition disc for dividing said needle chamber into a forward compartment and a rearward compartment with said needle carrier being disposed in said rearward compartment, said forward compartment being in fluid communication with said needle to permit flashback of blood into said forward compartment.

11. The catheter assembly of claim 10, wherein said needle includes a transverse aperture opening into said forward compartment.

12. An over-the-needle catheter assembly operable in a normal mode and convertible to a retraction mode, comprising:

an elongated, generally cylindrical needle chamber forming a hollow nozzle located at the distal end of the needle chamber and opening into the interior of the needle chamber, said needle chamber having a longitudinal slot formed in the cylindrical wall of said needle chamber, said needle chamber having a linear track therein;

a needle carrier slidably mounted on said linear track in the interior of said needle chamber for movement between a forward position and a retracted position, said needle carrier having a hollow needle mounted thereon, said needle protruding through said nozzle when said needle carrier is in said forward position, said needle being concealed by said needle chamber when said needle carrier is in said retracted position;

latch means coupled to said needle carrier through said longitudinal slot, said latch means being engaged to said needle chamber to lock said needle carrier in said forward position during the normal mode and being disengaged from said needle chamber during the retraction mode; and locking means for locking said needle carrier in said retracted position.

13. An over-the-needle catheter assembly operable in a normal mode and convertible to a retraction mode, comprising:

an elongated, generally cylindrical needle chamber forming a hollow nozzle located at the distal end of the needle chamber and opening into the interior of the needle chamber, said needle chamber having a longitudinal slot formed in the cylindrical wall of said needle chamber, said needle chamber having a linear track therein;

a needle carrier slidably mounted on said linear track within said needle chamber for movement between a forward position and a retracted position, said needle carrier having a hollow needle mounted thereon, said needle protruding through said nozzle when said needle carrier is in said forward position, said needle being concealed by said needle chamber when said needle carrier is in said retracted position;

latch means coupled to said needle carrier through said longitudinal slot, said latch means being engaged to said needle chamber to lock said needle carrier in said forward position during the normal mode and being disengaged from said needle chamber during the retraction mode, said latch means securing an over-the-needle catheter to said needle chamber during the normal mode; and locking means for locking said needle carrier in said retracted position.

14. The catheter assembly of claim 12, wherein said latch means includes a hinge pivotally mounted on said needle carrier, and wherein said hinge includes means for securing the hub of the over-the-needle catheter to said needle chamber to lock said needle carrier in said forward position during the normal mode.

15. The catheter assembly of claim 12, wherein said needle carrier includes a handle extending through said longitudinal slot and said latch means is connected to said handle, and wherein movement between said forward position and said retracted position is effected by corresponding movement of said handle through said longitudinal slot.

16. The catheter assembly of claim 14, wherein said securing means disengages the hub of the over-the-needle catheter from said needle chamber during the retraction mode.

17. The catheter assembly of claim 12, wherein said locking means includes a detente located on said needle carrier which engages with a mating detente located at the proximal end of said linear track.

18. An over-the-needle catheter assembly operable in a normal mode and convertible to a retraction mode, comprising:

an elongated, generally cylindrical needle chamber forming a hollow nozzle located at the distal end of the needle chamber and opening into the interior of the needle chamber, said needle chamber having a longitudinal slot formed in the cylindrical wall of said needle chamber, said needle chamber having a linear track therein;

a needle carrier slidably mounted on said linear track within said needle chamber for movement between a forward position and a retracted position, said needle carrier having a hollow needle mounted thereon, said needle protruding through said nozzle when said needle carrier is in said forward position, said needle being concealed by said needle chamber when said needle carrier is in said retracted position;

latch means coupled to said needle carrier through said longitudinal slot, said latch means being engaged to said needle chamber to lock said needle carrier in said forward position during the normal mode and being disengaged from said needle chamber during the retraction mode;

locking means for locking said needle carrier in said retracted position, and a transverse partition disc for dividing said needle chamber into a forward compartment and a rearward compartment with said needle carrier being disposed in said rearward compartment, said forward compartment being in fluid communication with said needle to permit flashback of blood into said forward compartment.

19. The catheter assembly of claim 18, wherein said needle includes a transverse aperture opening into said forward compartment.

20. An over-the-needle catheter assembly operable in a normal mode and convertible to a retraction mode, comprising:

an elongated, generally cylindrical needle chamber forming a hollow nozzle located at the distal end of the needle chamber and opening into the interior of the needle chamber, said needle chamber having a longitudinal slot formed in the cylindrical wall of said needle chamber;

a needle carrier slidably mounted within said needle chamber for movement between a forward position and a retracted position, said needle carrier having a hollow needle mounted thereon, said needle protruding through said nozzle when said needle carrier is in said forward position, said needle being concealed by said needle chamber when said needle carrier is in said retracted position;

latch means coupled to said needle carrier through said longitudinal slot, said latch means being engaged to said needle chamber to lock said needle carrier in said forward position during the normal mode and being disengaged from said needle chamber during the retraction mode, said latch means securing an over-the-needle catheter to said needle chamber during the normal mode;

locking means for locking said needle carrier in said retracted position; and a transverse partition disc for dividing said needle chamber into a forward compartment and a rearward compartment with said needle carrier being disposed in said rearward compartment, said forward compartment being in fluid communication with said needle to permit flashback of blood into said forward compartment.

21. The catheter assembly of claim 20, wherein said needle includes a transverse aperture opening into said forward compartment.

22. The catheter assembly of claim 21, wherein said needle chamber includes a linear track therein and said needle carrier is slidably mounted on said linear track.

23. The catheter assembly of claim 20, wherein said latch means includes a hinge pivotally mounted on said needle carrier, and wherein said hinge secures the hub of the over-the-needle catheter to said needle chamber to lock said needle carrier in said forward position during the normal mode.

24. The catheter assembly of claim 20, wherein said needle carrier includes a handle extending through said longitudinal slot and said latch means is connected to said handle, and wherein movement between said forward position and said retracted position is effected by corresponding movement of said handle through said longitudinal slot.

25. The catheter assembly of claim 23, wherein said hinge disengages the hub of the over-the-needle catheter from said needle chamber during the retraction mode.

26. The catheter assembly of claim 22, wherein said locking means includes a detente located on said needle carrier which engages with a mating detente located at the proximal end of said linear track.

27. An over-the-needle catheter assembly operable in a normal mode and convertible to a retraction mode, comprising:

a needle chamber forming a hollow nozzle located at the distal end of said needle chamber and opening into the interior of said needle chamber;

a needle carrier carrying a hollow needle on the distal end thereof, said needle carrier being slidably mounted in said needle chamber, said needle carrier detachably engaging said needle chamber with the distal portion of said needle carrier disposed within said nozzle of said needle chamber during the normal mode, said needle protruding through said nozzle when said needle carrier is in said forward position, said needle being concealed by said needle chamber when said needle carrier is in said retracted position;

a hollow tube rotatably mounted within said needle chamber, said needle carrier being disposed within said hollow tube;

an over-the-needle catheter mounted over said nozzle during the normal mode and disengaged from said nozzle during the retraction mode; and retraction means, responsive to rotation of said hollow tube, for disengaging said needle carrier from said needle chamber to switch the assembly from the normal mode to the retraction mode and for retracting said needle carrier into said hollow tube such that said needle is concealed within said needle chamber.

28. The catheter assembly of claim 27, wherein said retraction means includes retainer means for limiting rotation of said needle carrier relative to needle chamber in response to rotation of said hollow tube relative to said needle chamber.

29. An over-the-needle catheter assembly operable in a normal mode and convertible to a retraction mode, comprising:

a needle chamber forming a hollow nozzle located at the distal end of said needle chamber and opening into the interior of said needle chamber;

a needle carrier carrying a hollow needle on the distal end thereof, said needle carrier being slidably mounted in said needle chamber, said needle carrier detachably engaging said needle chamber with the distal portion of said needle carrier disposed within said nozzle of said needle chamber during the normal mode;

a hollow tube rotatably mounted within said needle chamber, said needle carrier being disposed within said hollow tube;

retraction means, responsive to rotation of said hollow tube, for disengaging said needle carrier from said needle chamber to switch the assembly from the normal mode to the retraction mode and for retracting said needle carrier into said hollow tube such that said needle is concealed within said needle chamber; and said retraction means including retainer means for limiting rotation of said needle carrier relative to needle chamber in response to rotation of said hollow tube relative to said needle chamber, said retraction means including a helical slot in said hollow tube, and said needle carrier including a side arm extending from said needle carrier through said helical slot, rotation of said hollow tube relative to said first chamber disengaging said needle carrier from said nozzle of said needle chamber and guiding said side arm of said needle carrier proximally through said helical slot, thereby retracting said needle carrier into said hollow tube.

30. The catheter assembly of claim 29, wherein said needle chamber includes a longitudinal slot, said side arm extending through said helical slot in said hollow tube and said longitudinal slot in said needle chamber, and wherein rotation of said hollow tube relative to said needle chamber guides said side arm proximally through said helical slot and said longitudinal slot, said longitudinal slot preventing said needle carrier from rotating relative to said needle chamber.

31. The catheter assembly of claim 27, wherein said needle carrier includes a tapered male luer at the distal end thereof, and wherein said male luer is detachably engaged within said nozzle by a taper lock.

32. The catheter assembly of claim 29, wherein said hollow tube includes a detente, disposed at the proximal end of said helical slot, for engaging said side arm to lock said needle carrier in a retracted position.

33. In an over-the-needle catheter assembly using an elongated needle chamber with a nozzle at the distal end thereof, a needle carrier slidably mounted on a linear track within the needle chamber for movement between a forward position and a retracted position, a needle mounted on the needle carrier, and a latch coupled to the needle carrier through a longitudinal slot in the needle chamber, the method comprising the steps of:

placing a catheter over the nozzle;

engaging the latch to the needle chamber to lock the needle carrier in the forward position;

disengaging the latch from the needle chamber to unlock the needle carrier from the forward position;

retracting the needle carrier on the linear track toward the proximal end of the needle chamber until the needle carrier is in the retracted position;

locking the needle carrier in the retracted position; and removing the catheter from the nozzle.

34. An over-the-needle catheter assembly operable in a normal mode and convertible to a retraction mode, comprising:

an elongated, generally cylindrical needle chamber forming a hollow nozzle located at the distal end of the needle chamber and opening into the interior of the needle chamber, said needle chamber having a longitudinal slot formed in the cylindrical wall of said needle chamber, said needle chamber having a linear track therein;

a needle carrier slidably mounted within said needle chamber for movement between a forward position and a retracted position, said needle carrier having a hollow needle mounted thereon, said needle protruding through said nozzle when said needle carrier is in said forward position, said needle being concealed by said needle chamber when said needle carrier is in said retracted position;

an over-the-needle catheter mounted over said nozzle during the normal mode and disengaged from said nozzle during the retraction mode;

latch means coupled to said needle carrier through said longitudinal slot, said latch means being engaged to said needle chamber to lock said needle carrier in said forward position during the normal mode and being disengaged from said needle chamber during the retraction mode, said latch means securing said over-the-needle catheter over said nozzle during the normal mode, said latch means being movable to disengage said over-the-needle catheter from said nozzle during the retraction mode while permitting said over-the-needle catheter to be separated from the remainder of the assembly for insertion into a vein of a patient; and locking means for locking said needle carrier in said retracted position.

35. The catheter assembly of claim 34, wherein said needle chamber includes a linear track therein and said needle carrier is slidably mounted on said linear track.

36. The catheter assembly of 35, wherein said locking means includes a detente located on said needle carrier which engages with a mating detente located at the proximal end of said linear track.

37. The catheter assembly of claim 34, wherein said latch means includes a hinge pivotally mounted on said needle carrier, and means for securing the hub of the over-the-needle catheter to said needle chamber to lock said needle carrier in said forward position during the normal mode.

38. The catheter assembly of claim 34, wherein said needle carrier includes a handle extending through said longitudinal slot and said latch means is connected to said handle, and wherein movement between forward position and said retracted position is effected by corresponding movement of said handle through said longitudinal slot.

39. The catheter assembly of claim 37, wherein said hinge is means for disengaging the hub of the over-the-needle catheter from said needle chamber during the retraction mode.

40. The catheter assembly of claim 37, wherein said hinge secures the hub of the over-the-needle catheter to the outer surface of said nozzle to lock said needle carrier in said forward position during the normal mode.

41. The catheter assembly of claim 34, further including a transverse partition disc for dividing said needle chamber into a forward compartment and a rearward compartment with said needle carrier being disposed in said rearward compartment, said forward compartment being in fluid communication with said needle to permit flashback of blood into said forward compartment.

42. The catheter assembly of claim 41, wherein said needle includes a transverse aperture opening into said forward compartment.

\* \* \* \* \*